(12) United States Patent
Shusterman

(10) Patent No.: US 11,207,028 B2
(45) Date of Patent: Dec. 28, 2021

(54) METHOD AND SYSTEM FOR MONITORING PHYSIOLOGICAL SIGNALS/HEALTH DATA, DEFIBRILLATION, AND PACING IN THE PRESENCE OF ELECTROMAGNETIC INTERFERENCE

(71) Applicant: Vladimir Shusterman, Pittsburgh, PA (US)

(72) Inventor: Vladimir Shusterman, Pittsburgh, PA (US)

( * ) Notice: Subject to any disclaimer, the term of this patent is extended or adjusted under 35 U.S.C. 154(b) by 107 days.

(21) Appl. No.: 16/260,098

(22) Filed: Jan. 28, 2019

(65) Prior Publication Data

US 2019/0159733 A1   May 30, 2019

Related U.S. Application Data

(63) Continuation-in-part of application No. 15/442,705, filed on Feb. 27, 2017, now Pat. No. 10,842,440, (Continued)

(51) Int. Cl.
*A61B 5/02* (2006.01)
*A61B 5/00* (2006.01)
(Continued)

(52) U.S. Cl.
CPC .......... *A61B 5/7203* (2013.01); *A61B 5/0002* (2013.01); *A61B 5/002* (2013.01); *A61B 5/0006* (2013.01); *A61B 5/0024* (2013.01); *A61B 5/0205* (2013.01); *A61B 5/055* (2013.01); *A61B 5/318* (2021.01); *A61B 5/7217* (2013.01); *A61B 5/7225* (2013.01); *A61N 1/3718* (2013.01); *A61N 1/3925* (2013.01); *G08C 17/02* (2013.01);
(Continued)

(58) Field of Classification Search
None
See application file for complete search history.

(56) References Cited

U.S. PATENT DOCUMENTS 5,187,657 A * 2/1993 Forbes ................. A61B 5/4812
600/513
5,730,146 A * 3/1998 Itil ......................... A61B 5/369
600/545

(Continued)

*Primary Examiner* — Sunit Pandya

(57) ABSTRACT

A system and method adapted for at least one health-related application selected from physiological monitoring, defibrillation, and pacing in the presence of electromagnetic interference (EMI) using the time-domain features of EMI patterns and physiological waveforms. The invention enables EMI detection and identification in a plurality of signals, including various physiological signals, which may contain both physiological information and EMI-generated artifacts. The system utilizes adaptive and versatile modular architecture with a set of modules for various filtering, conditioning, processing, and wireless transmission functions, which can be assembled in different configurations for different settings. In some preferred embodiments, the method and system of this invention are incorporated into (or attached to) an external cardiac defibrillator/monitor or cardiac pacing device. Other preferred embodiments include a wireless monitoring system that provides reliable wireless data transmission during patient table (bed) movement.

19 Claims, 25 Drawing Sheets

Related U.S. Application Data which is a continuation-in-part of application No. 14/470,923, filed on Aug. 27, 2014, now Pat. No. 9,610,016.

(60) Provisional application No. 62/622,996, filed on Jan. 29, 2018.

(51) Int. Cl.

| | | |
|---|---|---|
| *A61B 5/0205* | (2006.01) | |
| *G16H 40/63* | (2018.01) | |
| *A61N 1/39* | (2006.01) | |
| *A61B 5/055* | (2006.01) | |
| *A61N 1/37* | (2006.01) | |
| *A61B 5/318* | (2021.01) | |
| *G08C 17/02* | (2006.01) | |
| *G01R 33/42* | (2006.01) | |
| *A61B 5/0215* | (2006.01) | |
| *A61B 5/1455* | (2006.01) | |
| *A61B 5/026* | (2006.01) | |
| *A61B 5/0285* | (2006.01) | |
| *A61B 5/0295* | (2006.01) | |
| *A61B 5/053* | (2021.01) | |
| *A61B 5/024* | (2006.01) | |
| *A61B 7/04* | (2006.01) | |
| *A61B 5/021* | (2006.01) | |
| *G01R 33/567* | (2006.01) | |
| *A61B 5/369* | (2021.01) | |
| *A61B 5/389* | (2021.01) | |

(52) U.S. Cl.
CPC ............ *G16H 40/63* (2018.01); *A61B 5/021* (2013.01); *A61B 5/0263* (2013.01); *A61B 5/0285* (2013.01); *A61B 5/0295* (2013.01); *A61B 5/02152* (2013.01); *A61B 5/02433* (2013.01); *A61B 5/053* (2013.01); *A61B 5/14551* (2013.01); *A61B 5/14552* (2013.01); *A61B 5/369* (2021.01); *A61B 5/389* (2021.01); *A61B 5/7282* (2013.01); *A61B 7/04* (2013.01); *A61B 2562/0219* (2013.01); *G01R 33/42* (2013.01); *G01R 33/5673* (2013.01)

(56) References Cited

U.S. PATENT DOCUMENTS

| | | | | |
|---|---|---|---|---|
| 6,221,011 | B1* | 4/2001 | Bardy | G16H 50/30 600/300 |
| 6,753,783 | B2* | 6/2004 | Friedman | A61B 5/0002 324/207.11 |
| 7,508,307 | B2* | 3/2009 | Albert | G08B 1/08 340/506 |
| 8,137,270 | B2* | 3/2012 | Keenan | A61B 5/389 600/301 |
| 8,388,530 | B2* | 3/2013 | Shusterman | G16H 50/20 600/300 |
| 8,437,843 | B1* | 5/2013 | Kayyali | A61B 5/0024 600/544 |
| 8,781,563 | B2* | 7/2014 | Foo | A61B 5/1117 600/509 |
| 9,183,351 | B2* | 11/2015 | Shusterman | A61B 5/02055 |
| 10,055,549 | B2* | 8/2018 | Chung | G16H 50/20 |
| 2005/0165323 | A1* | 7/2005 | Montgomery | A61B 5/369 600/544 |
| 2006/0183980 | A1* | 8/2006 | Yang | G16H 20/70 600/301 |
| 2007/0010721 | A1* | 1/2007 | Chen | A61B 5/0002 600/300 |
| 2007/0288265 | A1* | 12/2007 | Quinian | G16H 10/60 705/2 |
| 2011/0004110 | A1* | 1/2011 | Shusterman | G16H 50/20 600/509 |
| 2013/0172691 | A1* | 7/2013 | Tran | G16H 50/20 600/301 |
| 2013/0231947 | A1* | 9/2013 | Shusterman | A61B 5/02055 705/2 |
| 2014/0081100 | A1* | 3/2014 | Muhsin | A61B 5/14551 600/324 |
| 2014/0213872 | A1* | 7/2014 | Rahman | G06F 1/08 600/372 |
| 2014/0266776 | A1* | 9/2014 | Miller | A61B 5/6849 340/870.01 |
| 2015/0106020 | A1* | 4/2015 | Chung | G16H 40/67 702/19 |

\* cited by examiner

ECG signals during real-time CMR scanning (2D SSFP sequence)—EMI filtering OFF

ECG signals during real-time CMR scanning (2D SSFP sequence)—EMI filtering ON

METHOD AND SYSTEM FOR MONITORING PHYSIOLOGICAL SIGNALS/HEALTH DATA, DEFIBRILLATION, AND PACING IN THE PRESENCE OF ELECTROMAGNETIC INTERFERENCE

This application is a continuation-in-part of pending U.S. patent application Ser. No. 15/442,705 filed on Feb. 27, 2017, which is a continuation-in-part of U.S. patent application Ser. No. 14/470,923 filed on Aug. 27, 2014 (now U.S. Pat. No. 9,610,016), which are incorporated herein by reference.

STATEMENT REGARDING FEDERALLY SPONSORED RESEARCH OR DEVELOPMENT

This invention was made with government support under contract HHSN268201400021C awarded by the National Institutes of Health. The government has certain rights in the invention.

BACKGROUND OF THE INVENTION

Field of the Invention

This invention relates to the field of monitoring medical and health data (e.g., vital signs, electrocardiogram, blood pressure, pulse oximetry, electroencephalogram) in the setting of magnetic resonance imaging (MRI) and MRI-guided procedures, X-ray and X-ray-guided procedures, and other sources of electromagnetic interference.

The following acronyms are used in this specification:
ABP—arterial blood pressure
A/D—analog-to-digital
CMR—cardiovascular magnetic resonance
CPLD—complex programmable logic device
DSP—digital signal processing
ECG—electrocardiogram/electrocardiographic
EEG—electroencephalogram
EMG—electromyogram
EMI—electromagnetic interference
FPGA—field programmable gate array
GMF—gradient magnetic field
GND—electrical ground
I-MRI—interventional magnetic resonance imaging
IV—intravenous
MHE—magneto-hydrodynamic effect
MR—magnetic resonance
PLD—programmable logic device
RF—radiofrequency
SNR—signal-to-noise ratio
SSFP—steady-state free precession
SVD—singular value decomposition
TE—time to echo
TR—time to repeat Physiological monitoring has become an essential part of health and disease management. A number of monitoring modalities, sensors, and systems have been developed for various settings and patient groups. They include in-hospital monitoring systems (e.g., bedside monitors and systems for patient monitoring during surgeries and other medical procedures) as well as out-of-hospital (ambulatory) and home monitoring systems. The most common types of collected information are electrocardiogram (ECG), electroencephalogram (EEG), electromyogram (EMG), temperature, respiration (breathing) rate and amplitude, oxygen saturation (pulse oximetry), arterial blood pressure (ABP), glucose, hemoglobin, physical activity, vascular resistance, and cardiac output.

The majority of in-hospital monitoring systems collect data from multiple sensors and/or channels. For example, cardiovascular hemodynamic monitoring often includes 12-lead ECG and 4 blood-pressure and pulse-oximetry channels; cardiac electrophysiological monitoring systems include at least 8 surface ECG channels and additional channels for collecting intracardiac electrograms, whereas EEG monitoring systems may incorporate up to 100 channels.

Systems for external cardiac defibrillation and pacing also require cardiovascular monitoring (e.g., ECG, blood pressure, pulse oximetry) in order to evaluate cardiac rhythm before and after defibrillation (electrical discharge or shock) or cardiac pacing, to detect cardiac arrhythmias (e.g., ventricular fibrillation, ventricular tachycardia, atrial fibrillation), or to perform a cardioversion (i.e., a synchronized shock delivered at a specific time point of the cardiac cycle, usually within the QRS complex on the ECG, which coincides with ventricular depolarization) or demand pacing, in which the patient's cardiac beats are monitored and pacing is inhibited when they are detected.

Because most physiological signals are relatively small and require frequent data sampling and real-time data transmission, both EMI and wireless data transmission represent major challenges for the development of such monitoring systems, as detailed below.

I. Electromagnetic Interference

Powerful sources of electromagnetic interference (EMI) that are usually present in a modern hospital environment can generate substantial amount of noise, distortion, and interference. The magnetic resonance imaging (MRI) scanner is an example of a powerful source of EMI, which can lead to signal artifacts that are several orders of magnitude greater than ECG or EEG signals. This interference becomes particularly important due to the requirement for high-fidelity, diagnostic ECG-monitoring during interventional cardiovascular MR (CMR) procedures and tracking subtle changes in the amplitude of the ECG ST segment and T wave, which may signal the earliest signs of ischemia in patients with coronary artery disease. Moreover, interventional CMR procedures also require rapid patient transportation (with continuous monitoring) between the MRI scanner room and X-ray room. Due to the requirement of continuous monitoring during both procedures, as well during transportation between the two rooms, a single wireless system must be used for this setting. The frequency of the signals generated by the MRI scanner's gradient magnetic fields (GMF interference) often overlaps with the frequency of cardiac signals (true ECG). In this situation, ECG signals represent a combination of the true ECG and GMF interference. Because the amplitude of MR gradients (GMF) is usually several orders of magnitude greater than the amplitude of the true ECG, MR-contaminated signals require substantial filtering, which modifies the pattern of the cardiac signals and diminishes its diagnostic value. In addition, the patterns of ECG signals in the presence of strong magnetic fields are changed by the magneto-hydrodynamic effect (MHE), which arises due to the circulation of magnetized blood in an individual's body. Although a number of filtering and reconstruction approaches have been developed to address this issue, an accurate, high-fidelity reconstruction of the diagnostic quality true-ECG signal remains a challenge (Wu et al. Adaptive noise cancellation to suppress electrocardiography artifacts during real-time interventional MRI. J Magnetic Resonance Imaging 33[5]: 1184-93 [2011]).

The prior-art approaches to the EMI filtering of physiological signals can be divided into three groups:

a. Approaches utilizing only/exclusively MR-gradient signals, which are either obtained directly from their sources (the MRI scanner or its control equipment) and which do not contain any physiological information (Odille et al. Noise cancellation signal processing method and computer system for improved real-time electrocardiogram artifact correction during MRI data acquisition. IEEE Trans Biomed Eng 54[4]:630-40 [2007]); additional "blanking" can be employed for preventing saturation of ECG amplifiers during the time periods of changes in MR gradients, which induce large artifacts in the ECG sensing cascades (Tse et al. A 1.5T MRI-conditional 12-lead electrocardiogram for MRI and intra-MR intervention. Magnetic Resonance in Medicine 71:1336-47 [2014]);

b. Methods utilizing dedicated, external antennas (coils, loops) for detecting changes in electromagnetic fields induced by MR gradients (Laudon et al. Minimizing interference from magnetic resonance imagers during electrocardiography. IEEE Trans Biomed Eng. 45[2]: 160-64 [1998]; Felblinger et al. Restoration of electrophysiological signals distorted by inductive effects of magnetic field gradients during MR sequences. Magnetic Resonance in Medicine 41:715-21 [1999]); and c. Approaches based on modeling ECG signals using the signals obtained outside the MRI scanner and relying on a simplified assumption that the ECG waveforms do not change during subsequent MR scanning (Oster et al. Nonlinear Bayesian filtering for denoising of electrocardiograms acquired in a magnetic resonance environment, IEEE Transactions on Biomedical Engineering 57[7]:1628-38 [2010]).

To summarize, the prior art approaches did not provide the detection of strong EMI (in particular GMF) in physiological signals using the properties of GMF waveforms and the differences between the GMF waveforms and physiological data. Therefore, to detect GMF, the prior-art methods and systems require a special source of GMF information (e.g., a cable connected to the MRI scanner or coil/antenna for the GMF detection).

II. Wireless Communication

Wireless connectivity offers mobility and convenience, which cannot be achieved using wire-based systems. In a hospital setting, this allows uninterrupted patient monitoring and movement of patients between different procedure/surgery rooms, intensive care units, emergency rooms, and hospital beds. In an out-of-hospital or home setting, wireless systems allow continuous monitoring during sleep and daily activities; they can also be used on the road and in other settings.

However, wireless data transmission poses several challenges compared with wire-based systems. First, the speed and rate of wireless data transmission are limited. This creates significant problems for the development of multi-channel/multi-sensor wireless systems (such as cardiac electrophysiological systems, cardiac hemodynamic monitoring, or EEG-mapping systems), which require significant data throughput. Furthermore, wireless systems are susceptible to electromagnetic noise and interference from external sources. This issue is particularly important for medical monitoring in the emergency setting and during interventional procedures, where uninterrupted, high-fidelity, real-time data are essential for patient diagnosis and management. The rapid proliferation of medical equipment with powerful electromagnetic sources (e.g., MRI scanners and X-ray machines) makes this issue particularly challenging in the modern hospital environment. Changing patient monitoring systems when a patient is moved for different diagnostic procedures and treatment throughout a hospital requires detachment and reattachment of multiple ECG leads and other sensors, adding a burden of time, effort, and cost for medical institutions and creating discontinuities (gaps) in patient monitoring.

Traditionally, wireless radiofrequency (RF) transmitters have been viewed as a simple replacement for wire-based data transmission. Thus, wireless system designs have essentially copied wire-based systems and added a single RF transmitter/receiver (Bluetooth, WiFi, Zigbee, cell phone, etc.). However, as explained above, this design strategy can lead to several problems. Specifically, a single RF transmitter has a limited data throughput, which may not be sufficient for multi-channel, high-sampling-rate data monitoring. Furthermore, wireless communication, using a single transmitter, can be significantly affected or completely interrupted by external EMI, potentially complicating patient management and outcomes in emergency settings, where transmission errors, delays, or interruptions may lead to delayed or inappropriate medical response and may be life threatening. This problem becomes even more difficult when the distance between the wireless radio transmitter and receiver changes during the transmission (for example, when the patient is being transported between two different procedure rooms while the data are transmitted wirelessly and are monitored in real time by physicians/nurses in a control room).

SUMMARY OF THE INVENTION

This invention further extends the EMI-filtering approach, described in the parent patent applications (Ser. Nos. 15/442,705 and 14/470,923), which uses time-domain features of EMI (in particular GMF) patterns and time-domain features of physiological waveforms to differentiate EMI patterns from physiological waveforms in the input signals.

In contrast to prior art, which requires a dedicated input channel for the GMF signal, the methods and systems of this invention are not limited to a dedicated input channel for GMF detection and identification (although the methods and systems of this invention can receive such GMF [or EMI] information using a dedicated channel such as a cable connection to an MRI scanner, a cable connection to the MRI gradient amplifiers, or a dedicated coil/antenna, if available).

Importantly, this invention enables EMI detection and identification in a plurality of signals, including various physiological signals, which may contain both physiological information and EMI-(or GMF-) generated artifacts. The signals are obtained using various types of physiological sensors, e.g., ECG electrodes, EEG electrodes, and other physiological sensors. As stated earlier, GMF detection is performed using the differences between features (e.g., $1^{st}$ time derivative, $2^{nd}$ time derivative, amplitude, time intervals between the waveform peaks, time intervals between the peaks of the time derivatives, time intervals between the peaks of the time derivatives and waveform peaks) of the GMF and physiological waveforms. For example, the derivatives of the GMF are usually substantially higher than those for physiological signals (e.g., the ECG R wave). Because the method and system of this invention provide GMF recognition and filtering within various physiological and non-physiological signals, which may have multiple sources (components), it can also provide GMF detection in a GMF-dedicated channel (a direct cable connection to an MRI scanner or a dedicated coil/antenna, if available).

In contrast to prior art, which usually captures GMF information directly from its source (an MRI scanner or an output from the scanner's magnetic-field gradient amplifiers), the methods and systems of this invention enable the detection of GMF interference captured by various sensors (e.g., ECG sensors) away from the GMF source. The GMF interference captured by physiological sensors and detected by the methods and systems of this invention may contain patterns of GMF interference that are different from GMF patterns generated by an MRI scanner. For example, this invention enables the detection of GMF interference in the signals captured by ECG sensors, which contain the $1^{st}$ time derivative of the GMF waveforms generated by an MRI scanner.

The methods and systems of this invention, which can be implemented using analog electronics and circuitry, digital electronic elements (e.g., the firmware installed in a microcontroller, field programmable gate array [FPGA], programmable logic device [PLD], or complex programmable logic device [CPLD], computer software), or combination thereof, include two or more of the following features:

a. One or more input sensors (e.g., ECG electrodes, coil/antenna, or a cable connection to the MRI scanner or its control unit);

b. One or more RF filters to eliminate the RF interference generated by the MRI scanner (e.g., a filter with a stop band at 64 MHz for a 1.5 T MRI scanner or at 124 MHz for a 3 T MRI scanner);

c. One or more EMI (in particular GMF) detectors, using the time-varying features of the EMI (in particular GMF) patterns (e.g., the $1^{st}$ time derivative, the $2^{nd}$ time derivative, amplitude, time intervals between the peaks and/or time derivatives) and the differences between the features of GMF waveforms and those of physiological signals (e.g., ECG or cardiac electrophysiology signals); the GMF detector may include an edge (i.e., time-derivative) detector and/or an amplitude (level) detector, as well as a signal-averaging element, which provides an average reference level for the EMI (in particular GMF) edge and/or level detectors.

d. A short delay line (e.g., 50 microseconds) for holding the input signals to provide the time required for GMF detection described above;

e. A switch that either passes collected physiological data or stops (discards) the data containing GMF;

f. A sample-and-hold element, which keeps the most recent value before the EMI (in particular GMF) was detected and the corresponding data segment was discarded;

g. A filter for filtering remaining noise and EMI from physiological data that were passed to the filter from the previous steps; the filter characteristics may be tuned (adjusted) to eliminate the frequencies that contain GMF (or EMI) and retain physiological information, which usually contains lower frequencies than GMF (e.g., setting the low-pass filter cutoff frequency to 300 Hz would retain the ECG waveforms, whose frequency is <150 Hz, but filter out the GMF, whose frequency is above 300 Hz).

h. One or more control elements for adjusting one or more parameters of the EMI (in particular GMF) detection, selected from:

1. Edge-detection threshold (time derivative) for detecting the EMI (in particular GMF);
2. Level-detection threshold (amplitude) for detecting the EMI (in particular GMF);
3. One or more control elements for adjusting one or more "dead-time" intervals during which the system returns to the original state after the EMI (in particular GMF) detection; this time determines the length of the data segment that is discarded after the EMI (in particular GMF) detection; and
4. One or more control elements for adjusting one or more time intervals between two time-domain features of the EMI pattern (e.g., the EMI pattern/waveform, peak of the $1^{st}$ time derivative of the EMI waveform, peak of the $2^{nd}$ time derivative of the EMI waveform, peaks of higher derivatives of the EMI waveform).

This invention provides a way to use a single system for patient monitoring during various interventional procedures (including X-ray- and MR-guided procedures), eliminating the need for multiple detachments/reattachments of various monitoring systems when the patient is moved from one room/procedure to another. In particular, the system of the present invention enables high-fidelity, wireless, multisensor monitoring in diagnostic suites (e.g., the interventional cardiology suite) and treatment units (e.g., intensive care unit), as well as during patient transportation between different procedures, units, hospitals, and clinics.

This invention is also useful for external cardiac defibrillation and pacing also require cardiovascular monitoring (e.g., ECG, blood pressure, pulse oximetry) in order to evaluate cardiac rhythm before and after defibrillation (electrical discharge or shock) or cardiac pacing, to detect cardiac arrhythmias (e.g., ventricular fibrillation, ventricular tachycardia, atrial fibrillation), or to perform a cardioversion (i.e., a synchronized shock delivered at a specific time point of the cardiac cycle, usually within the QRS complex on the ECG, which coincides with ventricular depolarization) or demand pacing, in which the patient's cardiac beats are monitored and pacing is inhibited when they are detected.

In some preferred embodiments, the method and system of this invention are incorporated into (or attached to, or housed together with) an external cardiac defibrillator/monitor (e.g., LifePak 20, Physio-Control, Redmond, Wash.), as disclosed in Shusterman U.S. Patent Application 62/490,031. In other preferred embodiments, the method and system of this invention can be connected by cable or cables to an external defibrillator and/or cardiac pacing device.

The system utilizes adaptive and versatile modular architecture with a set of modules for various filtering, conditioning, processing, and wireless transmission functions, which can be assembled in different configurations for different settings. In some preferred embodiments, the method and system of this invention are incorporated into (or attached to) an external cardiac defibrillator/monitor or cardiac pacing device. Other preferred embodiments include a wireless monitoring system that provides reliable wireless data transmission during patient table (bed) movement. To achieve reliable, real-time transmission of large volumes of data, some embodiments of the invention employ one or more wireless transmitters.

As explained above, the powerful EMI generated by the MRI systems contaminates physiological signals and necessitates data filtering. In particular, filtering is required to remove GMF interference, whose frequency spectrum often overlaps with that of the ECG signals and whose magnitude may be substantially higher than that of the ECG signals.

Because the system of the present invention is mobile and wireless, it preferably should not have any physical connection to the MRI scanner or its control equipment, which are commonly used as a source of information about MR gradients. Instead, the system of this invention utilizes the electrodes, associated cables/electronic circuitry, and the body of a monitored individual as a receiving antenna and circuitry for detecting, filtering, and analyzing features and patterns of EMI. In particular, the system of the present invention separates GMF interference from physiological signals, using a-priori information (criteria) about differences of these signals' characteristics. These include differences in time-domain features (e.g., amplitude, derivatives, area, integral and waveform patterns) and frequency-domain features (dominant frequency and frequency range). The criteria are adjusted using the measurements performed at different distances from the magnet (i.e., at different strengths of magnetic field) in the presence and/or absence of working MR gradients, as detailed in the Description of the Preferred Embodiments.

The system of present invention also reconstructs physiological signals in the presence of strong MHE, using the measurements performed at different distances from the magnet (i.e., at different strengths of magnetic field), and changes in blood flow and blood pressure, which affect the magnitude of MHE.

To summarize, the system of the present invention includes the following innovative features:

a. Multiple filterbanks (filtering procedures) for recording both diagnostic-quality (broad-band) signals in the absence of EMI and filtered-out (narrow-band) signals in the presence of EMI, with subsequent reconstruction of diagnostic-quality signals from the filtered-out signals using the transfer matrices (reconstruction coefficients) obtained and/or fine-tuned at the initial (calibration) stages of data recording;

b. Filtering of EMI (in particular GMF interference) using a-priori information (criteria) about differences between the GMF and physiological signals' characteristics. The criteria are adjusted using measurements performed at different distances from the magnet (i.e., at different strengths of magnetic field) in the presence and/or absence of working MR gradients;

c. Filtering of the MHE, using physiological measurements at different distances from the magnet (i.e., at different strengths of magnetic field), and changes in blood flow and blood pressure, which affect the magnitude of MHE.

d. One or more wireless transmitters for increasing the reliability and speed (throughput) of the wireless data transmission, which is critically important for large volumes of continuous, multichannel data.

One important aspect of this invention is mounting (linking/connecting) a wireless antenna to a movable/wheeled patient table (herein, the terms patient table, bed, and procedure table are used interchangeably) to enable reliable wireless data transmission at different locations of the patient table and during its movement in the course of various procedures, as well as between different procedures and/or rooms. An important aspect of this invention is the positioning of one or more antennas connected to a wireless transmitter and one or more antennas connected to a wireless receiver (herein referred to as the first and second antenna, respectively) to provide a free (unobstructed) plane (space) for substantially continuous wireless communication between the two antennas at various positions of the patient table and during table movement.

The wireless system of this invention, which provides monitoring of the health data of an individual lying on a movable/wheeled patient table, includes:

one or more acquisition modules with one or more sensors adapted to be placed on an individual's skin for collecting one or more physiological signals by substantially continuous monitoring of the individual's health data, and one or more wireless transmitters for substantially continuous transmission of one or more physiological signals; and one or more wireless transmitters having one or more first antennas linked to the patient table to receive one or more physiological signals from the acquisition module and transmitting the signals substantially continuously from various locations and during movement of the patient table and the individual;

wherein one or more first antennas are positioned to provide substantially unobstructed communication to one or more second antennas on a receiver regardless of the location of the patient table and the movement of medical personnel around the table.

An important aspect of this invention is adapting digital signal processing (DSP) operations based on the properties of EMI and cardiac-activity waveforms as described below.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Signal Filtering and Reconstruction in the Presence of EMI

The system of the present invention utilizes one or more of the following approaches implemented using DSP and/or analog electronics:

I. MR-Gradient Detector

Figure 2:
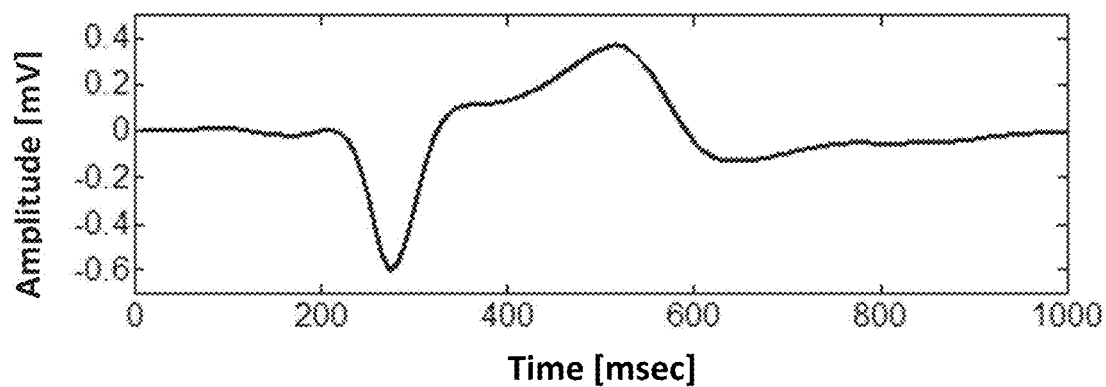
FIG. 2 is an example of an ECG signal (Lead II) recorded in a human subject outside an MRI scanner.
Figure 3:
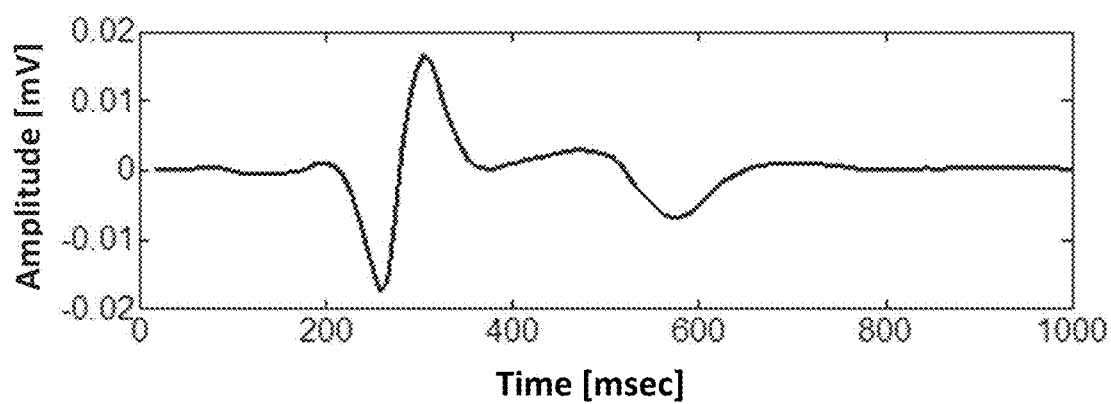
FIG. 3 is the time derivative of the ECG signal in FIG. 2.

In most pulse sequences employed in modern MR scans, MR gradients generate voltages with magnitudes and derivatives which are substantially higher than those of electrophysiological signals (e.g., ECG, EEG, EMG). FIGS. 2 and 3 show an example of an ECG signal and its time derivative, respectively; the ECG was recorded in a human subject before an MRI scan. The ECG signal has the maximum range of approximately 1 mV, and the range of the derivative is approximately 0.04 mV/ms.

Figure 4:
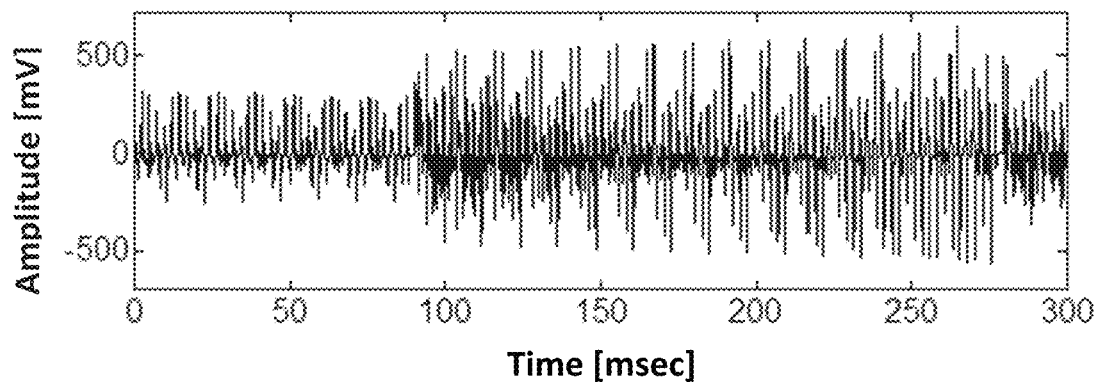
FIG. 4 is an example of GMF interference in electrophysiological recordings obtained during a short time-to-echo (TE)/time-to-repeat (TR) pulse sequence, which is commonly used in interventional CMR procedures. The raw, unamplified signal was recorded using surface ECG electrodes, which were attached to the precordial chest region (corresponding to the ECG lead II position).
Figure 5:
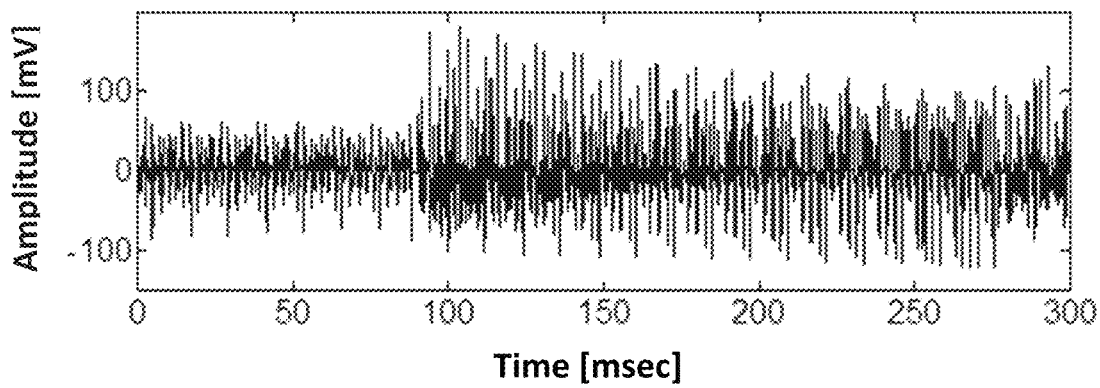
FIG. 5 is the time derivative of the GMF-interference signal in FIG. 4.

FIG. 4 shows an example of GMF interference in electrophysiological recordings obtained during a short-TE/TR pulse sequence, which is commonly used in interventional CMR procedures. The signal was recorded using surface ECG electrodes, which were attached to the precordial chest region (corresponding to the ECG lead II position). FIG. 5 shows the time derivative of the GMF-interference signal in FIG. 4. Because the amplitude of GMF and its time derivative are several orders of magnitude greater than those of ECG signals, its amplitude and time derivative are used by the GMF detector to discriminate between the GMF and physiological (e.g., ECG, EEG, EMG) signals. The threshold values can be set constant or adapted (adjusted, fine-tuned, optimized) automatically or manually, using the ECG signals obtained before the MR scan. In addition, the dominant frequency of the GMF signals (>80 Hz) is usually higher than the dominant frequency of the ECG signals (approximately 30-60 Hz). In other words, the rise-time of the GMF signals is shorter than that for the ECG signals. Therefore, in different configurations of methods and systems of this invention, the GMF detector also utilizes the signal's dominant frequency, rise-time, absolute magnitude (range) and/or its time derivatives (e.g., $1^{st}$ and $2^{nd}$ derivatives), waveform pattern, and other signal characteristics.

As stated earlier, the methods and systems of this invention provide GMF detection without the need for a separate, dedicated input channel providing for the GMF (or EMI) signal. While the methods and systems of this invention can receive such GMF (or EMI) information using a dedicated channel (a cable connection to the GMF source, e.g., an MRI scanner, its gradient-amplifier unit [cabinet], or a dedicated coil/antenna, if available), they can also use other signal types which do not originate from the GMF-generating source (e.g., MRI scanner) and which may include physiological signals obtained from an individual's body using various types of physiological sensors. The sensors (e.g., ECG, EMG, or EEG electrodes) may be attached (or located in close proximity) to the body of an individual (human or animal subject) or may remain unattached. For example, the GMF interference encountered in the ECG signal represents the $1^{st}$ time derivative of the magnetic-field gradients generated by an MRI scanner.

The signals obtained from physiological sensors may contain both physiological information (waveforms) and GMF-generated patterns (artifacts). As stated earlier, GMF detection is performed using the differences between time-domain features (e.g., $1^{st}$ time derivative, $2^{nd}$ time derivative, amplitude, time intervals between the peaks, time intervals between the peaks of the time derivatives, time intervals between the peaks of the time derivatives and waveform peaks) of the GMF patterns and physiological waveforms. For example, the derivatives of the GMF are usually substantially higher than those for physiological signals (e.g., the ECG R wave).

The data-acquisition, filtering, and processing module/cascade (whose various implementations are shown in FIGS. 6-11) can be implemented using analog electronics and circuitry, digital electronic elements (e.g., the firmware installed in a microcontroller, FPGA, PLD, CPLD, computer software), or a combination thereof.

Example Data-Acquisition and Processing Module

The data-acquisition and processing module/cascade includes the following principal elements (FIG. 12):

a. One or more sensors adapted for collecting one or more input signals containing physiological data from the body of an individual. For example, the input sensors 1201 may include ECG electrodes to obtain one or more input signals from an individual's body, wherein the input signals may contain physiological (ECG) data and EMI (in particular, GMF interference) generated by an MRI scanner. As stated above, the GMF interference picked up by the ECG electrodes and cables represents the $1^{st}$ time derivative of the GMF generated by an MRI scanner. Examples of other sensors include EEG, EMG, blood-pressure, pulse-oximetry, and accelerometer sensors. In some embodiments, the input sensors 1201 may be also located in close proximity to an individual's body but do not touch it. In other embodiments, the input sensors 1201 may be connected to the source of EMI (in particular GMF), such as an MRI scanner or an output of its gradient amplifier unit/cabinet.

b. One or more EMI detectors (e.g., EMI edge detector 1203, EMI level detector 1204) for identifying EMI waveforms within one or more input signals using one or more time-domain features (e.g., $1^{st}$ time derivative, $2^{nd}$ time derivative, waveform amplitude, peak amplitude of the $1^{st}$ time derivative, peak amplitude of the $2^{nd}$ time derivative) of the EMI waveforms, whose range is different from that of the time-domain feature of the physiological data; and c. One or more processing elements for minimizing the EMI within the time intervals in which the EMI waveforms are detected.

Various embodiments of the processing elements may include one or more of the following elements, as shown in the example implementation of the data-acquisition and processing circuitry (FIG. 12):

a. One or more RF filters 1202 having the cutoff frequency respecting the Larmor frequency at the specific magnetic field strength of the MRI scanner (~64 MHz at 1.5 T, ~128 MHz at 3 T, ~300 MHz at 7 T, ~400 MHz at 9 T, or ~500 MHz at 11 T) to eliminate the RF interference generated by the MRI scanner (e.g., a low-pass filter with a cutoff frequency<64 MHz, the Larmor frequency for a 1.5 T MRI scanner; a low-pass filter with a cutoff frequency<128 MHz for a 3 T MRI scanner; a notch filter with a stop band at 64 MHz for a 1.5 T MRI scanner; or a notch filter with a stop band at 128 MHz for a 3 T MRI scanner). In some embodiments, RF filters 1202 could also be band-pass filters, whose upper cutoff frequency is below the Larmor frequency, and the lower cutoff frequency is above the low frequencies that require filtering (e.g., 0.05 Hz baseline wander).

b. One or more EMI (in particular GMF) detectors, using the time-varying features of the EMI (in particular GMF) waveforms/patterns (e.g., the amplitude of the $1^{st}$ time derivative, the amplitude of the $2^{nd}$ time derivative, the amplitude of the EMI waveform, the time interval between the peak of the EMI waveform and its time derivative, or the time interval between the peaks of the $1^{st}$ time derivative and the $2^{nd}$ time derivative of the EMI waveform), as well as the differences between the features of GMF waveforms and those of physiological signals (e.g., ECG or cardiac electrophysiology signals). The GMF detector may include:

1. One or more EMI edge (i.e., the $1^{st}$ time-derivative of the EMI waveform picked up by ECG electrodes, which is equivalent to the $2^{nd}$ time-derivative of the GMF generated by an MRI scanner) detectors 1203,
2. One or more amplitude (level) detectors 1204,
3. One or more signal-averaging elements 1205 to provide one or more signal average values (reference levels) for the EMI (in particular GMF) level detector 1204.

c. One or more short delay lines 1207 (e.g., 50 microseconds) for holding the input signals during the time required for GMF detection by the GMF detectors 1203 and/or 1204 described above;

d. One or more logical elements 1208 (e.g., a logical gate or an open collector) for receiving the outputs from two or more EMI detectors 1203 and 1204, and generating a binary output ("EMI detected: switching OFF" or "no EMI detected: staying ON," as shown in 1209), which controls one or more switches 1210. The logical element 1208 stays in the "no EMI detected: staying ON" state as long as no EMI is detected by either EMI detector 1203 or 1204; and the element 1208 switches to the "EMI detected: switching OFF" state when EMI is detected by one or more EMI detectors 1203 or 1204;

e. One or more "sample-and-hold" elements 1210, which include at least one switch (1211) with two states controlled by the logical element 1208: "ON" or "OFF." In the ON state (when no EMI is detected by the element 1208), switch 1211 passes the input data/signal to a data-collection unit 1214. In the OFF state (when EMI is detected by the logical element 1208), switch 1211 shorts the circuit to discard the data segment whose length is determined by the "switch-ON" delay (which is controlled by one or more control elements 1217). The sample-and-hold element 1210 (e.g., a capacitor connected to large-value resistors to slow the capacitor's discharge) keeps the most recent value before the EMI (in particular GMF) was detected in the input data and the corresponding data segment was discarded;

f. One or more filters 1213 (referred to as the "main" filter in FIG. 12) for filtering residual noise and EMI from physiological data that were passed to the filter from the previous steps; the filter characteristics may be tuned (adjusted) to filter out the frequencies that contain EMI (which are usually higher than the frequencies containing physiological data) and retain the lower frequencies, which contain physiological information. (For example, setting the low-pass filter cutoff frequency to 300 Hz would retain the ECG waveforms, whose frequency is <150 Hz, but filter out the GMF, whose frequency is above 300 Hz.) The filter 1213 passes the data to one or more data-collection elements 1214.

g. One or more control elements for adjusting one or more parameters of the EMI (in particular GMF interference) detection, selected from:

1. One or more control elements 1215 of the EMI (in particular GMF) edge-detection threshold ($1^{st}$ time derivative of the input data). As noted above, the GMF interference picked up by the ECG electrodes contains the $1^{st}$ derivative of the GMF generated by an MRI scanner. Thus, if the ECG sensors are used as input sensors 1201, the control 1215 regulates the $2^{nd}$ time-derivative threshold for detecting GMF generated by the scanner.

2. One or more control elements 1216 of the EMI (in particular GMF) level (amplitude)-detection threshold;

3. One or more control elements 1217 regulates the switching-ON delay time for the switch 1210 after the logical element 1208 switches to the "EMI detected: switching OFF" state. Note that control elements 1217 affects only the switch-ON delay, whereas the switching-OFF delay (when EMI is detected) occurs instantaneously (without any delay). Therefore, control elements 1217 effectively determines the duration of the discarded data segment (the "dead" time between the switching-OFF and switching-ON state); and 4. One or more control elements (not shown) of the time intervals between two or more time-domain features of the EMI pattern (e.g., peaks of the EMI waveform, peak of the $1^{st}$ time derivative of the EMI waveform, peak of the $2^{nd}$ time derivative of the EMI waveform).

Figure 12:
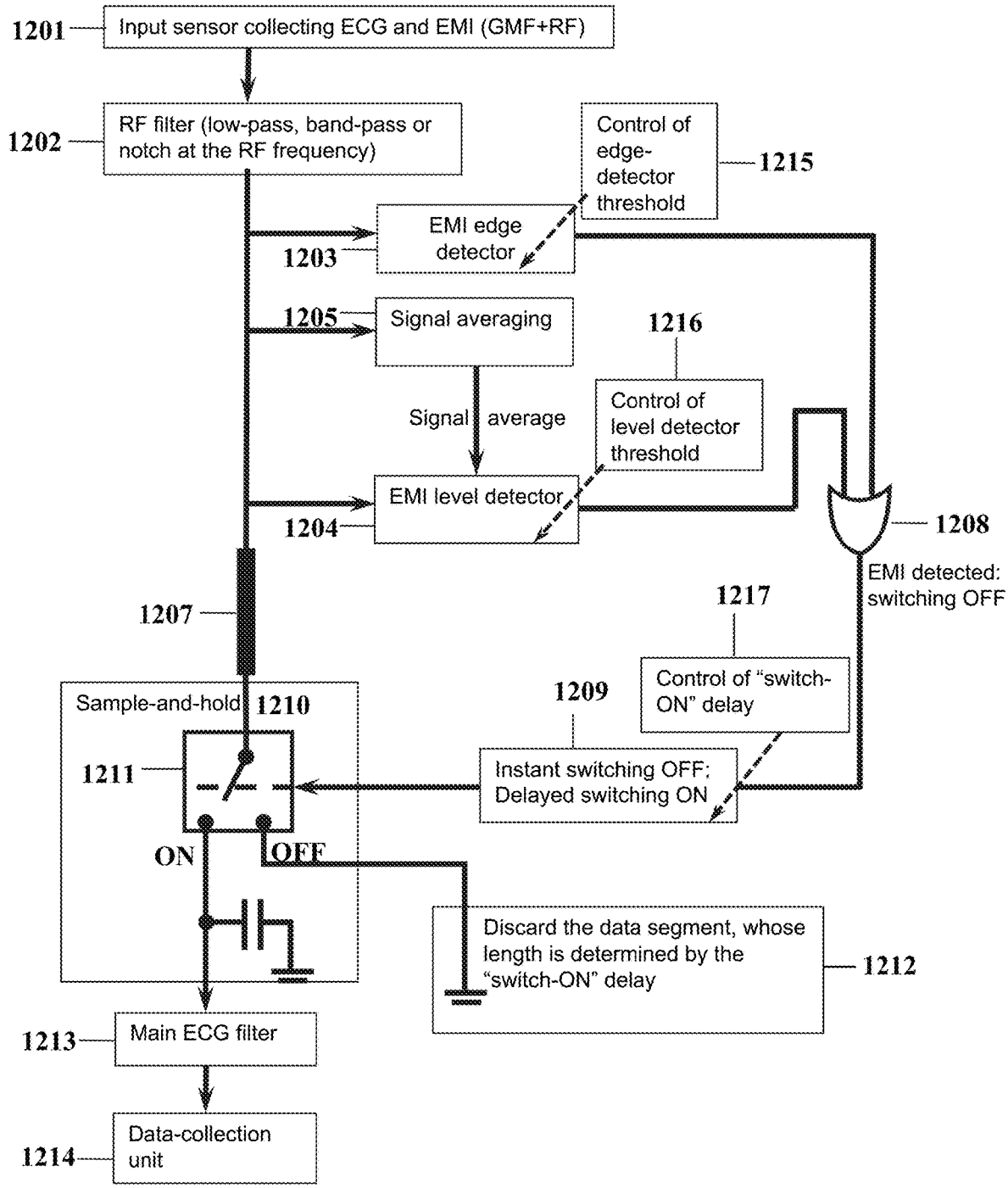
FIG. 12 is a block diagram of an example implementation of the data-acquisition and processing circuitry.

The example implementation of the data-acquisition and processing circuitry shown in FIG. 12 and described above provides either complete elimination (blanking) of EMI waveforms (EMI patterns/artifacts) or partial elimination of EMI waveforms (dipping or attenuation), depending on the properties of EMI waveforms (e.g., time derivative, amplitude, duration, duty cycle) and selected signal-processing parameters (e.g., EMI detection thresholds in EMI detectors 1203 and/or 1204, duration of the delay provided by the delay line 1207).

EMI blanking is achieved if the following three conditions are satisfied:

a. The time derivative of the EMI leading edge is greater than the detection threshold of the EMI edge detector 1203, or the level (average value) of the EMI waveform is greater than the detection threshold of the EMI level detection 1204;

b. the time interval between the onset of EMI waveforms and the detection of those EMI waveforms by EMI detectors (e.g., 1203 and/or 1204) is smaller than the delay provided by the delay line 1207 (e.g., 50 microseconds in the example described above), and c. the duration of the EMI waveforms is shorter than the combined delay of: 1) the delay line 1207 and 2) the switching-ON delay time (i.e., the dead time) for the switch 1210.

If only the first condition (condition a) described above is satisfied, the example implementation of the data-acquisition and processing circuitry shown in FIG. 12 and described above provides partial blanking or clipping (attenuation) of the EMI waveforms.

Various embodiments of the processing elements may include one or more of the following elements, as shown in the example implementation of the data-acquisition and processing circuitry (FIG. 13):

a. One or more RF filters 1302 having the cutoff frequency respecting the Larmor frequency at the specific magnetic field strength of the MRI scanner (~64 MHz at 1.5 T, ~128 MHz at 3 T, ~300 MHz at 7 T, ~400 MHz at 9 T, or ~500 MHz at 11 T) to eliminate the RF interference generated by the MRI scanner (e.g., a low-pass filter with a cutoff frequency<64 MHz, the Larmor frequency for a 1.5 T MRI scanner; a low-pass filter with a cutoff frequency<128 MHz for a 3 T MRI scanner; a notch filter with a stop band at 64 MHz for a 1.5 T MRI scanner; or a notch filter with a stop band at 128 MHz for a 3 T MRI scanner). In some embodiments, RF filters 1302 could also be band-pass filters, whose upper cutoff frequency is below the Larmor frequency, and the lower cutoff frequency is above the low frequencies that require filtering (e.g., 0.05 Hz baseline wander).

b. One or more EMI (in particular GMF) detectors, using the time-varying features of the EMI (in particular GMF) waveforms/patterns (e.g., the amplitude of the $1^{st}$ time derivative, the amplitude of the $2^{nd}$ time derivative, the amplitude of the EMI waveform, the time interval between the peak of the EMI waveform and its time derivative, or the time interval between the peaks of the $1^{st}$ time derivative and the $2^{nd}$ time derivative of the EMI waveform), as well as the differences between the features of GMF waveforms and those of physiological signals (e.g., ECG or cardiac electrophysiology signals). The GMF detector may include:

1. One or more EMI edge (i.e., the $1^{st}$ time-derivative of the EMI waveform picked up by ECG electrodes, which is equivalent to the $2^{nd}$ time-derivative of the GMF generated by an MRI scanner) detectors 1303,
2. One or more EMI amplitude (level) detectors 1304,
3. One or more signal-averaging elements 1305 to provide one or more signal average values (reference levels) for the EMI (in particular GMF) level detector 1304.

c. One or more short delay lines 1307 (e.g., 50 microseconds) for holding the input signals during the time required for GMF detection by the GMF detectors 1303 and/or 1304 described above;

d. One or more differential-amplifier elements 1308 (e.g., an instrumentation amplifier or an operational amplifier with associated circuitry), which has two inputs ("+" and "−") and one output. The "+" input of 1308 receives the output signal from the delay line 1307 and the "−" input of 1308 receives one or more reference signals received from switch 1324.

e. One or more switches 1324 with two states: "ON" or "OFF." In the ON state (when EMI is detected by the EMI level-detector 1304), switch 1324 passes the reference value obtained by the signal averaging element 1305 to the "−" input of the differential amplifier 1308, which subtracts the reference (voltage) value from the delay-line 1307 output voltage, producing a differential output signal, and passes it to one or more sample-and-hold elements 1310. In the OFF state (when EMI is not detected by the EMI level-detector 1304), switch 1324 disconnects the "−" input of 1308 from the signal-averaging element 1305 and connects it to the electrical GND. As a result, the differential amplifier 1308 passes single-ended output signal to the sample-and-hold element 1310 when switch 1324 is switched OFF.

f. One or more sample-and-hold elements 1310 (e.g., a capacitor connected to large-value resistors to slow the capacitor's discharge) for keeping the most recent data (signal) value. The sample-and-hold element 1310 may include one or more switches 1311, which have two states: "ON" and "OFF". In the ON state (when no EMI is detected by the EMI edge detector 1303), switch 1311 passes the input data/signal to a data-collection unit 1314. In the OFF state (when EMI is detected by the EMI edge detector 1303), switch 1311 shorts the circuit to discard the data segment. The length of discarded data segment is determined by the "switch-ON" delay (which is controlled by one or more control elements 1317). The sample-and-hold element 1310 keeps the most recent value before the EMI (in particular GMF) was detected in the input data by the EMI edge detector 1303;

g. A filter 1313 (referred to as the "main" filter in FIG. 13) for filtering residual noise and EMI from physiological data that were passed to the filter from the previous steps; the filter characteristics may be tuned (adjusted) to filter out the frequencies that contain EMI (which are usually higher than the frequencies containing physiological data) and retain the lower frequencies, which contain physiological information. (For example, setting the low-pass filter cutoff frequency to 300 Hz would retain the ECG waveforms, whose frequency is <150 Hz, but filter out the GMF, whose frequency is above 300 Hz.) The filter 1313 passes the data to one or more data-collection elements 1314.

h. One or more control elements for adjusting one or more parameters of the EMI (in particular GMF interference) detection, selected from:

5. One or more control elements 1315 of the EMI (in particular GMF) edge-detection threshold ($1^{st}$ time derivative of the input data). As noted above, the GMF interference picked up by the ECG electrodes contains the $1^{st}$ derivative of the GMF generated by an MRI scanner. Thus, if the ECG sensors are used as input sensors 1301, the control 1315 regulates the $2^{nd}$ time-derivative threshold for detecting GMF generated by the scanner.
6. One or more control elements 1306 of the EMI (in particular GMF) level (amplitude)-detection threshold;
7. One or more control elements 1317 regulate the switching-ON delay time for the switch 1311 after the "EMI detected: switching OFF" state of the sample-and-hold element 1310. Note that control element 1317 affects only the switch-ON delay, whereas the switching-OFF delay (when EMI is detected) occurs instantaneously (without any delay). Therefore, control element 1317 effectively determines the duration of the discarded data segment (the "dead" time between the switching-OFF and switching-ON state); and
8. One or more control elements (not shown) of the time intervals between two or more time-domain features of the EMI pattern (e.g., peaks of the EMI waveform, peak of the $1^{st}$ time derivative of the EMI waveform, peak of the $2^{nd}$ time derivative of the EMI waveform).

Figure 13:
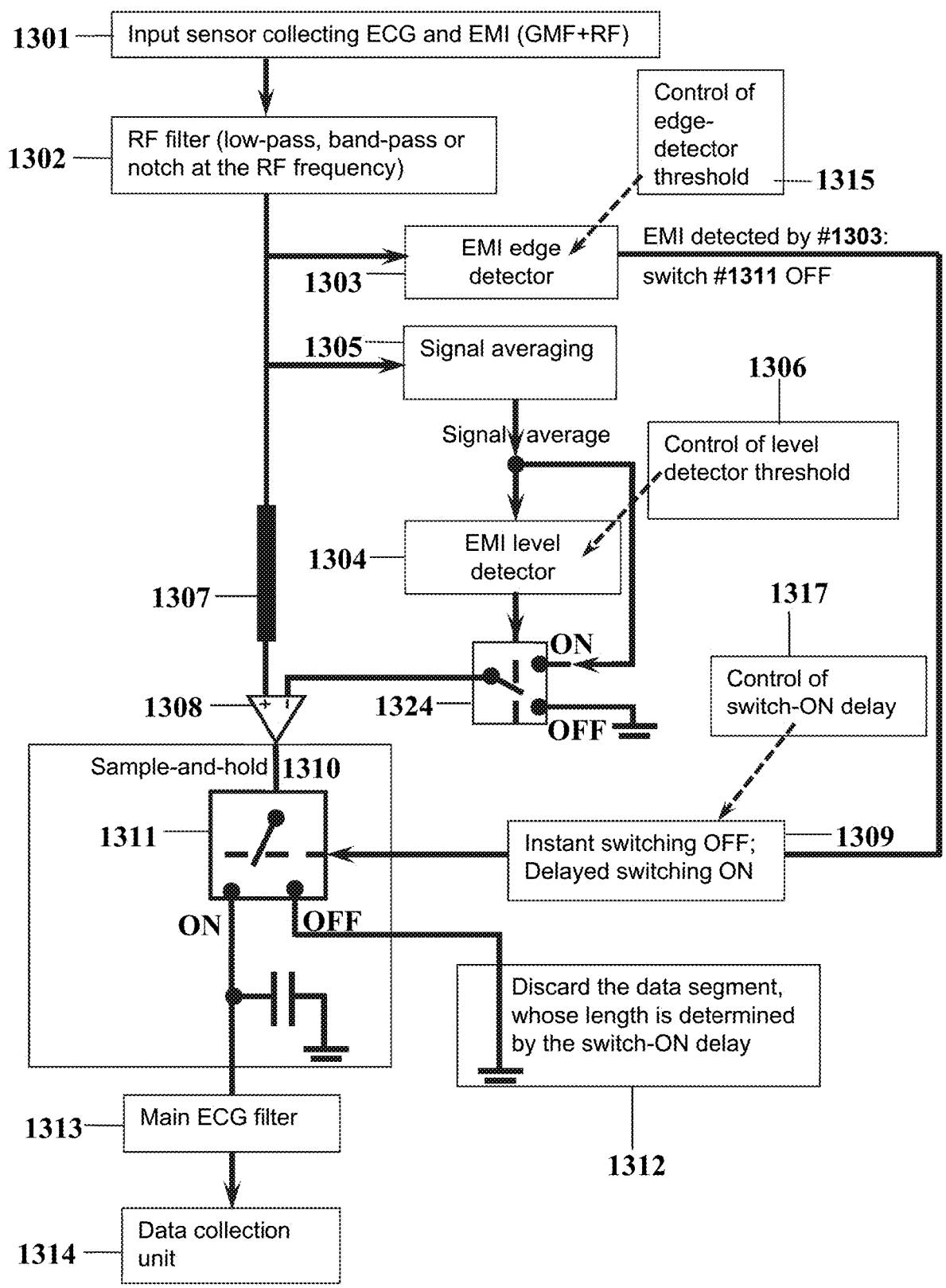
FIG. 13 is a block diagram of another example implementation of the data-acquisition and processing circuitry.
Figure 14:
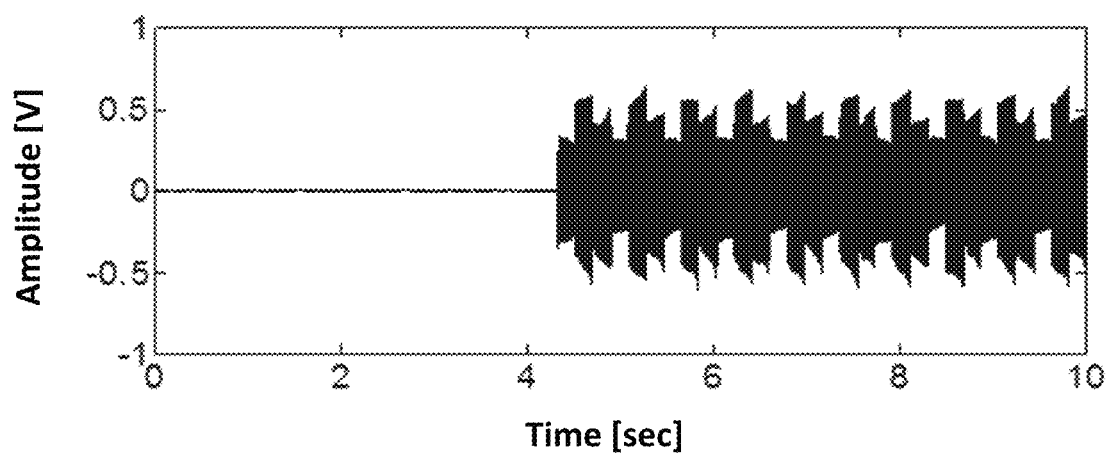
FIG. 14 is an example of a raw (unamplified and unfiltered) signal that was recorded using surface ECG electrodes (corresponding to ECG lead II). The MR scanning was initiated approximately 4 sec after the beginning of the recording and was associated with large-amplitude GMF interference.
Figure 15:
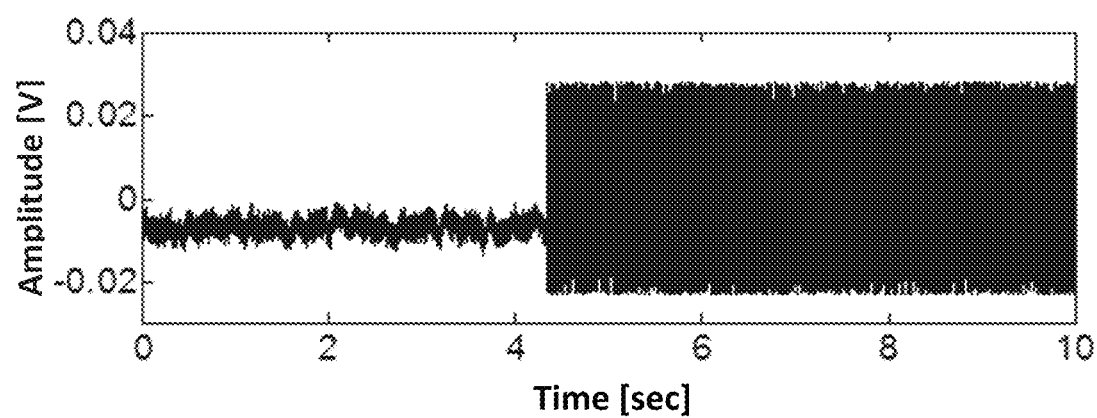
FIG. 15 shows application of a bitwise "shift-left" operation to the signal in FIG. 14. The amplitude of the GMF interference decreased approximately 50 times.

The example implementation of the data-acquisition and processing circuitry shown in FIG. 13 and described above provides either complete elimination (blanking) of EMI waveforms (EMI patterns/artifacts) or partial elimination of EMI waveforms (dipping or attenuation), depending on the properties of EMI waveforms (e.g., time derivative, amplitude, duration, duty cycle) and selected signal-processing parameters (e.g., EMI detection threshold in the EMI edge detector 1303, duration of the delay provided by the delay line 1307).

EMI blanking is achieved if the following three conditions are satisfied:

a. The time derivative of the EMI leading edge is greater than the detection threshold of the EMI edge detector 1303,
b. the time interval between the onset of EMI waveforms and the detection of those EMI waveforms by the EMI edge detector 1303 is smaller than the delay provided by the delay line 1307 (e.g., 50 microseconds in the example described above), and c. the duration of the EMI waveforms is shorter than the combined delay of: 1) the delay line 1307 and 2) the switching-ON delay time (i.e., the dead time) for the switch 1311.

If only the first condition (condition a) described above is satisfied, the example implementation of the data-acquisition and processing circuitry shown in FIG. 13 and described above provides partial blanking or clipping (attenuation) of the EMI waveforms.

If the EMI's derivative (edge, slope) is smaller than the detection threshold of the EMI edge detector 1303, such EMI will not be detected by detector 1303. In this case, the EMI can be detected by the level detector 1304 and filtered (subtracted) from the signal by the differential amplifier element 1308 with the switch 1324.

In some preferred embodiments, the data-acquisition and processing cascade described above and shown in FIG. 12 and FIG. 13 can be implemented as a stand-alone printed circuit board (PCB), which may be connected to other PCBs. In other preferred embodiments, the data-acquisition and processing cascade described above and shown in FIG. 12 and FIG. 13 can be implemented as a stand-alone device, or as part of a device that includes other functions. For example, the data-acquisition and processing cascade described above and shown in FIG. 12 and FIG. 13 can be incorporated into (or attached to, or housed with) an external cardiac defibrillator and/or cardiac pacing device to evaluate cardiac rhythm before and after defibrillation (electrical discharge or shock) or cardiac pacing, to detect cardiac arrhythmias ventricular fibrillation, ventricular tachycardia, atrial fibrillation), or to perform a cardioversion (i.e., a synchronized shock delivered at a specific time point of the cardiac cycle, usually within the QRS complex on the ECG, which coincides with ventricular depolarization) or demand pacing, in which the patient's cardiac beats are monitored and pacing is inhibited when they are detected.

Example systems of this invention may include various combinations of the data-acquisition, processing, filtering, conditioning, and wireless transmission modules described in the specification and shown in FIGS. 1, 6-13, and 23-29.

Example systems of this invention may use a wireless and/or non-wireless (e.g., USB cable) connection for transferring the data to a PC without delay (which is inherent for wireless transmission at 2.4 or 5.2 GHz). In some preferred embodiments, the system utilizes the data-acquisition and processing circuitry disclosed on FIG. 12 and FIG. 13 to minimize the EMI generated by the GMFs of an MRI scanner.

The filtering and conditioning module, in particular the data-acquisition and processing cascade described above, may be implemented in a microcontroller (e.g., Texas Instruments, MSP-430), a microprocessor (e.g., Texas Instruments KEYSTONE, ARM CORTEX, C6000, Intel CORE i7 or ATOM, or an ATMEL ARM CORTEX processor), an FPGA (e.g., Xilinx SPARTAN FPGA, Xilinx VIRTEX FPGA, or Altera Cyclone FPGA), a CPLD, a system-on-chip, or a general-purpose personal computer.

The systems and methods of this invention may further include a second processing module to provide one or more additional filtering and processing operations. The second processing module may include a wireless radio receiver for receiving data from the sensor and/or processing module, which may be connected to a wireless radio transmitter (e.g., a 2.4 GHz wireless transmitter such as Wi-Fi, Bluetooth, or ZigBee radio).

II. Filtering GMF Using Parallel Filterbanks

The system of the present invention employs two or more banks of filters (filterbanks) or DSP filtering procedures, which are selected using a mechanical, electronic, or software-controlled (programmable) switch. Filterbank I allows recording of gold-standard, diagnostic-quality physiological signals, using the settings specified in the appropriate performance standards (e.g., diagnostic ECG signals using a frequency band of 0.05-250 Hz, as specified in ANSI/AAMI EC11:1991/(R)2007 "Diagnostic electrocardiographic devices"). However, Filterbank I cannot effectively filter out GMF interference, which often overlaps with the spectrum of the ECG signals. Filterbank II is designed for filtering out GMF interference (e.g., using a low-pass, $8^{th}$-order Butterworth filter with a 40-Hz 3 dB cutoff frequency) but does not provide the bandwidth required for diagnostic ECG evaluation of the cardiac waveforms (e.g., changes in the ST segment and T wave).

Block diagrams of several configurations of a medical device of this invention with different types of arrangements of the filterbanks and GMF detector are shown in FIGS. 6-11.

The switchable filterbanks allow clinicians to use a single monitoring system for various procedures with different levels of EMI. For example, Filterbank I can be used to obtain diagnostic ECG in environments with relatively low levels of EMI, e.g., during the course of X-ray guided cardiovascular procedures, patient transport, and bedside monitoring. Switching from Filterbank I to Filterbank II allows uninterrupted data monitoring in environments with a high level of EMI, such as MRI.

In addition, switchable filterbanks are useful for efficient filtering and reconstruction of physiological signals, as described below.

III. Filtering GMF Using Time-Domain GMF Features

Because GMF interference is several orders of magnitude greater than cardiac electrical activity, it may cause saturation of amplifiers and/or filters in monitoring systems' electronic circuitry.

The utility of frequency-domain filtering of GMF interference is limited by an overlap between the frequency ranges of physiological signals (e.g., ECG has a frequency range of 0.05-250 Hz) and GMF interference (80-1000 Hz). In addition, the amplitude and derivative of the GMF signal are several orders of magnitude greater than those for physiological signals, and with respect to the low-amplitude/ derivative physiological signals, it can be approximated by Dirac delta or Heaviside step function (the integral of the delta function). The frequency power spectrum of the delta function has a constant amplitude and broad distribution (spans all frequencies). Therefore, time-domain approaches implemented in DSP and/or analog electronics are beneficial for filtering GMF signals, as shown below. They include bitwise operations combined with voltage division and/or multiplication, pattern recognition, template matching, and wavelet-based filtering tailored to characteristics and/or patterns of the GMF signals.

Figure 11:
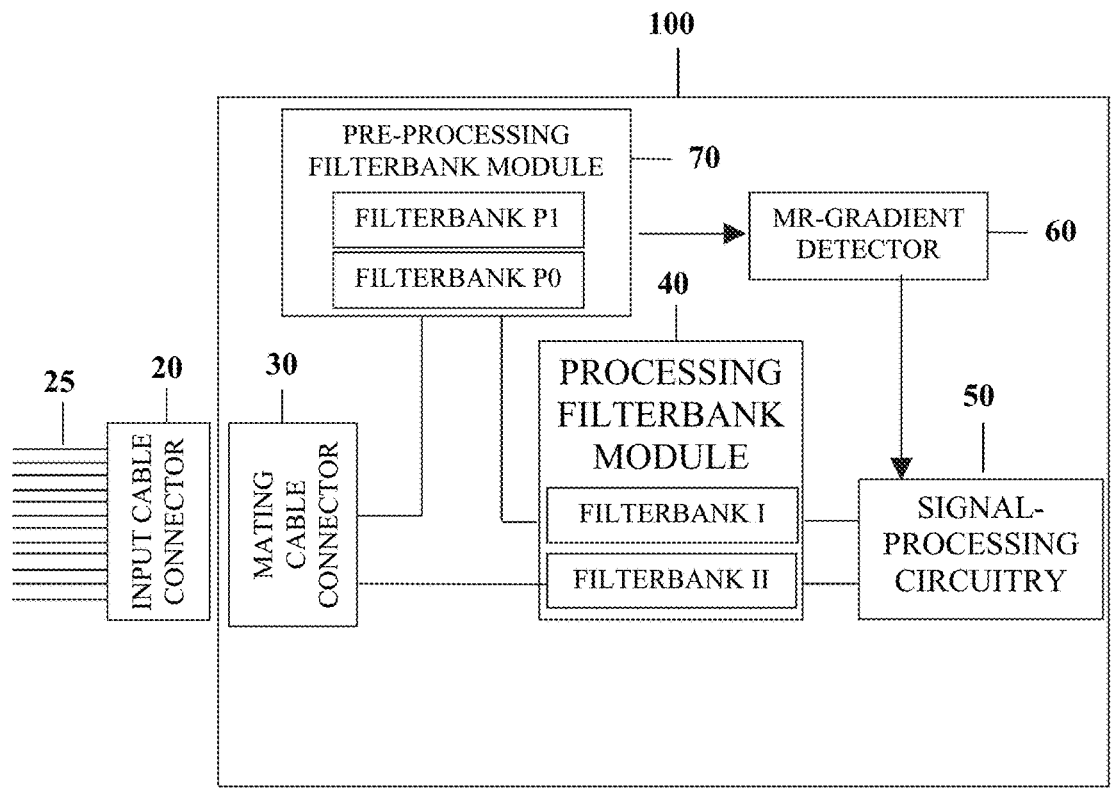
FIG. 11 is a block diagram of the system configuration, which includes a pre-processing filterbank module 70 with Filterbank P1 and Filterbank P0.

In one embodiment of the present invention, voltage division is applied to the "raw," unfiltered signals as the first, pre-processing step, in order to prevent amplifier saturation (FIG. 11). This pre-processing step is required for data collection during an MR scan using Filterbank I (see above). The system of the present invention includes a set of two pre-processing filterbanks or filtering procedures (Filterbank P1 and Filterbank P0) that can be switched using an electronic, mechanical, or software-controlled (programmable) switch. Filterbank P1 includes voltage-dividing resistors, whereas Filterbank P0 includes only "zero-Ohm" resistors or simple wires. When Filterbank P1 is switched on, the signals undergo voltage division, which is usually associated with an increased amount of signal noise, which can be filtered using analog or programmable filters.

This signal conditioning using bitwise operations includes the following operations:

a. To filter out the GMF signal, the most significant bits are discarded, because the high-amplitude GMF signal is predominantly contained in the most significant bits. This is achieved using a bitwise "shift-left" operation (which is analogous to voltage multiplication) and discarding the "uppermost" (most significant) bits. In one embodiment of the present invention, this operation is implemented using a DSP. In another embodiment it is implemented using an amplifier (or a charge pump) to multiply the signal, a comparator for checking the resulting voltage, an operational amplifier for subtracting the part of the signal that exceeds a certain threshold, and an analog-to-digital (A/D) converter. In a third embodiment, the operation is implemented using and A/D converter with serial control (e.g., Texas Instruments TLC2543C, TLC2543I, or TLC2543M), in which the uppermost bits are discarded.

b. Similarly, to extract a "clean" GMF signal, the least significant (rightmost) bits are discarded. This is achieved using a bitwise "shift-right" operation (analogous to voltage division). In different embodiments of the present invention, this operation is implemented using a DSP, an A/D converter with serial control (e.g., Texas Instruments TLC2543C, TLC2543I, or TLC2543M) in which the least significant bits are discarded, or analog circuitry (utilizing resistors or charge pumps for voltage division), as described above. Subtracting the resulting "clean" GMF signal from the original ("raw") signals produces a "clean" physiological (ECG) signal and vice versa.

c. Filtering procedures (low-pass, high-pass, notch, or band-pass) are applied to the output signal obtained after the bit-shift operation above.

Figure 16:
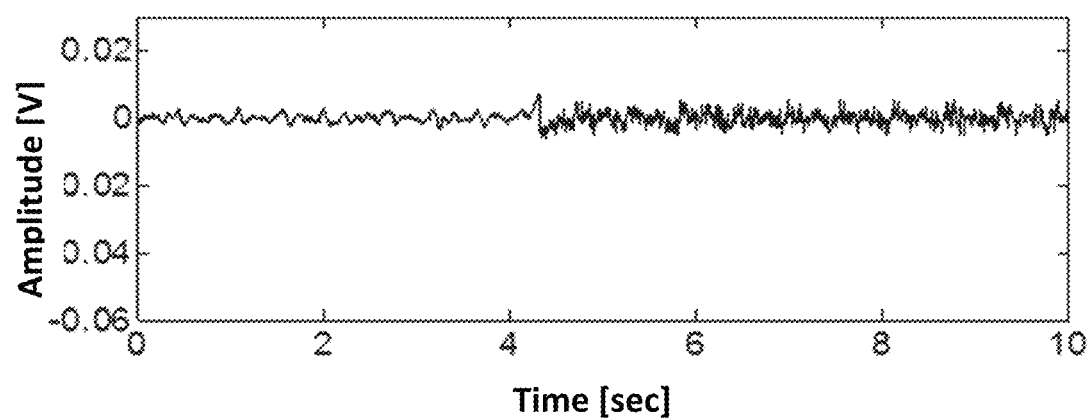
FIG. 16 shows application of subsequent band-pass filtering ($4^{th}$ order band-pass Butterworth filter with a 1-60 Hz pass-band) applied after the bitwise "shift-left" operation in FIG. 15.
Figure 17:
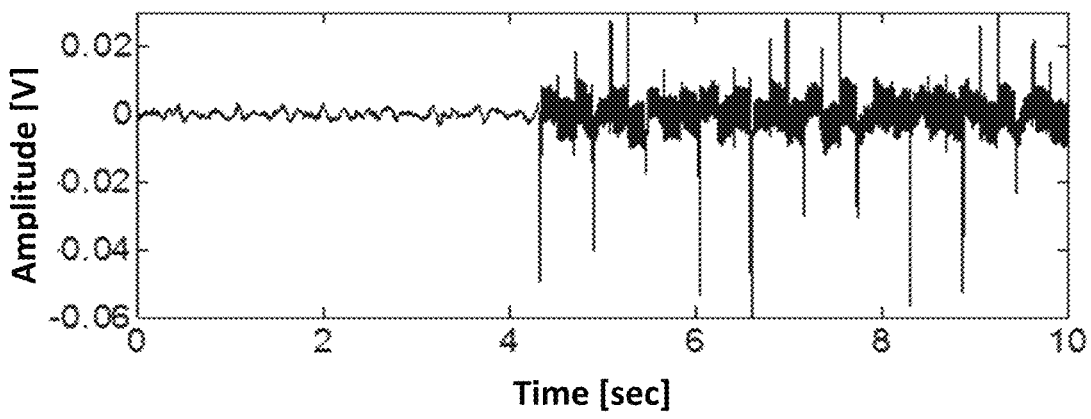
FIG. 17 shows application of the same band-pass filtering as in FIG. 16, which was applied to the original signal (i.e., bypassing the bitwise shift operation shown in FIG. 15). Note that the low-amplitude signals are identical during the first 4 sec of the recordings (before the MR scan). However, during the MR scan, the two-step conditioning procedure described above (FIGS. 15 and 16) provides a substantially cleaner signal (i.e., smaller interference) compared with the simple band-pass filtering shown in FIG. 17.

FIGS. 14-17 show an application of this procedure for filtering of GMF interference from electrophysiological recordings obtained during real-time SSFP pulse sequence with short TR (TR=2.44-2.7 ms) and TE (TE=1.22-1.35 ms), which are commonly used in interventional CMR. The raw (unamplified and unfiltered) signal shown in FIG. 14 was recorded using surface ECG electrodes, which were attached to the precordial chest region (corresponding to the ECG lead II position) of a subject. MR scanning was initiated approximately 4 sec after the beginning of the recording and was associated with large-amplitude GMF interference. A bitwise "shift-left" operation decreased the amplitude of the GMF interference approximately 50 times (FIG. 15), but did not affect the low-amplitude patterns, which were represented in the least-significant ("rightmost") bits. FIG. 16 shows an application of subsequent band-pass filtering (the $4^{th}$ order, band-pass Butterworth filter with a 1-60 Hz pass-band) applied after the bitwise "shift-left" operation, whereas FIG. 17 shows application of the same band-pass filtering procedure applied to the original signal (i.e., without prior bitwise shift operation). Note that the low-amplitude signals are identical during the first 4 sec of the recordings (before the MR scan). However, during the MR scan, the two-step conditioning procedure described above (FIG. 16) provides substantially cleaner signal (i.e., smaller interference), as compared with simple band-pass filtering (FIG. 17).

IV. Filtering GMF and MHE Using Signal Reconstruction

Filtering GMF interference and reconstructing ECG waveforms (or other physiological signals) includes the following steps (and their variations):

A. To obtain clean, diagnostic ECG signals, a diagnostic ECG is recorded using Filterbank I outside the MR bore.

B. Keeping the subject's position and the distance from the magnet unchanged, a second (non-diagnostic) ECG is recorded using Filterbank II.

C. For each ECG lead, patient-specific transfer coefficients b are computed between the diagnostic ECG signal (waveform), y, recorded in section A (above) and the corresponding non-diagnostic ECG signal, X, recorded in section B, as a solution to a linear regression problem. Specifically, for each ECG-lead, y=X+e, where b are the regression weights or coefficients that need to be determined and e are measurement errors. Omitting the measurement errors e in order to find an approximate form of the solution, $$b=(X^TX)^{-1}X^Ty,$$

where $X^T$ denotes X transposed. The two signals (waveforms), X and y, are synchronized using the fiducial points (e.g., the ECG R peak) or maximum cross-correlation between the two signals. This method works reasonably accurately when the measurement errors e are small and can be neglected.

However, in a real-life setting, the measurement errors e are relatively large, and the measured signal often contains a significant amount of noise. To minimize the magnitude of noise, the present invention utilizes the truncated singular value decomposition (SVD) of a square matrix, $\tilde{X}^T\tilde{X}$, which is constructed from the measured signal, $\tilde{X}$, as a time-aligned series of physiological events (e.g., using the R peaks of consecutive cardiac complexes in the ECG signal), and $\tilde{X}^T$ denotes $\tilde{X}$ transposed. The SVD is equivalent to the Principal Component Analysis and Karhunen-Loeve decomposition, which represent linear orthogonal decompositions, in which the basis vectors (eigenvectors or eigenfunctions) with the smallest weights (eigenvalues) are truncated. The truncation is based on the idea that the eigenvectors associated with the largest eigenvalues correspond to the measured signal, whereas those associated with small eigenvalues correspond to measurement noise (Shusterman U.S. Pat. Nos. 8,388,530; 7,801,591 and 7,485,095; Odille et al. Noise cancellation signal processing method and computer system for improved real-time electrocardiogram artifact correction during MRI data acquisition. IEEE Transactions on Biomedical Engineering 54[4]:630-40 [2007]), $$X^+(\tilde{X}^T\tilde{X})^{-1}\tilde{X}^T=(U\Sigma V^T)^{-1}\tilde{X}^T=(V\Sigma^{-1}U^T)\tilde{X}^T\sim(V\tilde{\Sigma}^{-1}U^T)\tilde{X}^T$$

where $X^T$ is the transpose of X and $\tilde{\Sigma}$ is the truncated SVD of the diagonal matrix $\Sigma$ of singular values (eigenvalues), in which the singular values that are less than a certain threshold are set to zero, reducing the rank of the associated matrix $(V\tilde{\Sigma}^{-1}U^T)$, which yields the following estimate of the regression coefficients:

$$b\sim(V\tilde{\Sigma}^{-1}U^T)\tilde{X}^Ty.$$

The properties of this linear orthogonal transform are well established. In particular, it is known that the transform provides a least-squares solution using the smallest number of the basis vectors associated with the largest eigenvalues (Shusterman U.S. Pat. Nos. 8,388,530; 7,801,591 and 7,485,095). This procedure is similar to signal averaging, which is also used to reduce the impact of noise in the method of the present invention.

D. The patient is moved inside the MR magnet bore, and the signals (e.g., ECG, EEG, EMG, blood pressure, pulse oximetry) are recorded using Filterbank I. The signals are affected by the MHE due to the circulation of magnetized blood in the patient's body. These signals are referred to as the MHE-ECG, MHE-EEG, MHE-EMG, MHE-pressure, etc.

E. Keeping the patient position unchanged inside the magnet bore, the signals are recorded using Filterbank II.

F. A patient-specific transfer matrix is constructed between the signals recorded in sections D and E above. The two signals (waveforms) are synchronized using the fiducial points (e.g., the ECG R peak) or maximum cross-correlation between the two signals, as described above. For each ECG lead, patient-specific transfer coefficients are calculated between the diagnostic ECG signal recorded in section A and the corresponding non-diagnostic ECG signal recorded in section B, using linear regression and truncated SVD, as described above (see section C).

G. During the MR scan, Filterbank II is used to filter out interference generated by the MR-gradients in real time. Then the diagnostic MHE-ECG is reconstructed using the patient-specific transfer matrix as described in section F above. To evaluate reconstruction accuracy, the reconstructed MHE-signals are compared with those recorded using Filterbank I in the absence of MR-gradients (when the scanning is not performed), as described in section D above, using cross-correlation and/or other statistical metrics.

If the reconstruction accuracy needs to be further increased, the process of computing the transfer matrix $X^+$ is treated as a minimization problem, with the goal (objective function) of minimizing the difference (and/or maximizing cross-correlation) between the two signals, using one or more methods selected from optimization algorithms. The optimization methods include simplex algorithm, iterative methods (e.g., Newton's method and quasi-Newton method, finite-difference method, and other methods of approximation theory and numerical analysis, methods that evaluate gradients using finite differences, sequential quadratic programming, approximate Hessians, gradient-descent or steepest-descent methods, ellipsoid method, simultaneous perturbation stochastic approximation, interpolation methods, and global convergence methods) and heuristic algorithms (e.g., memetic algorithm, differential evolution, differential search, dynamic relaxation, genetic algorithms, Hill climbing, Nelder-Mead algorithm, reactive search optimization).

H. To reconstruct a clean (free of MHE), diagnostic ECG, the reconstructed signals described in section G above are multiplied by the corresponding transfer matrix described in section C above. The reconstruction accuracy is evaluated by comparing reconstructed diagnostic, clean signals with those measured directly (see section A above), using cross-correlation and/or other statistical metrics. If the reconstruction accuracy is not sufficiently high, the process of computing the transfer matrix $X^+$ is treated as a minimization problem, with the goal (objective function) of minimizing the difference (and/or maximizing the cross-correlation) between the two signals, using one or more methods described in section G above.

Figure 18:
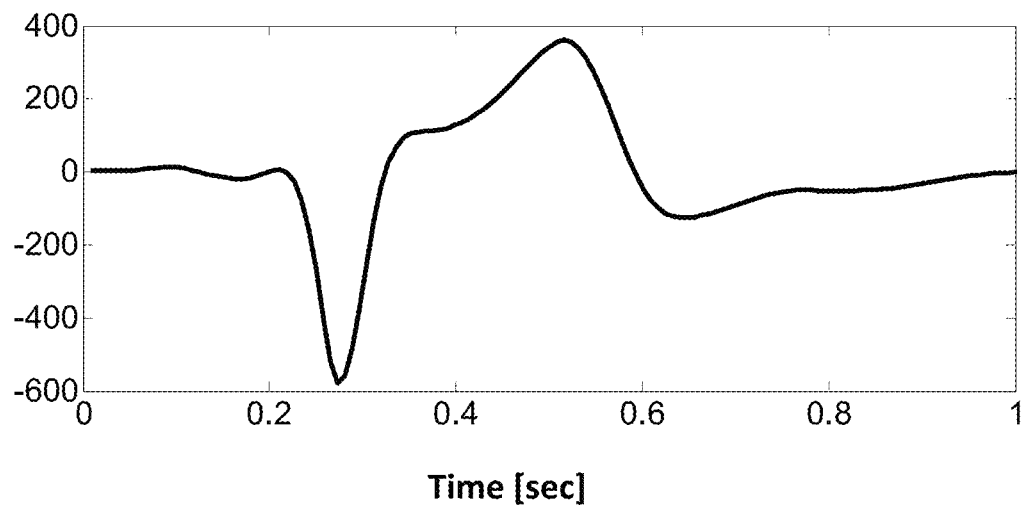
FIG. 18 is an example of a clean diagnostic ECG signal (Lead II) recorded outside the magnet bore.
Figure 19:
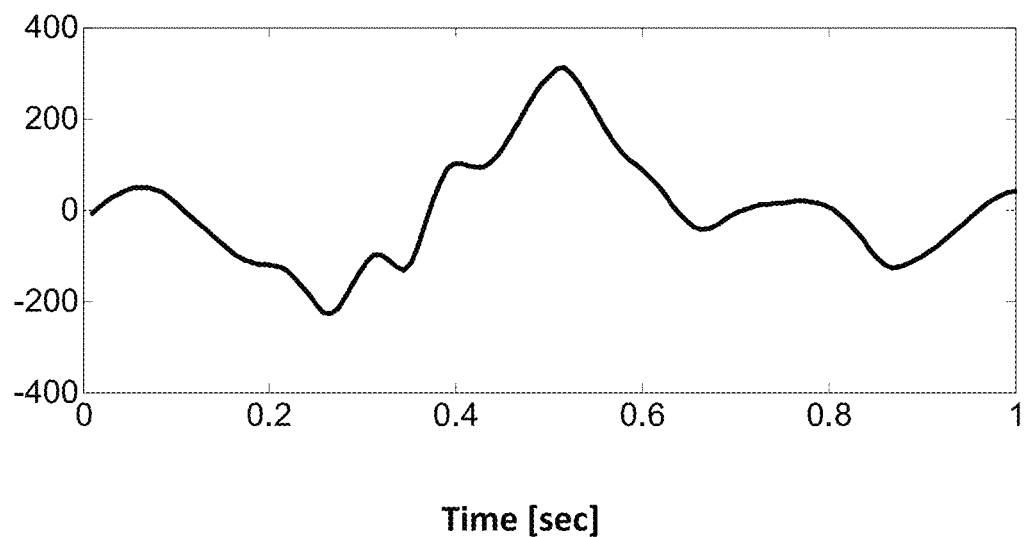
FIG. 19 is the signal in the same ECG lead after the subject was moved inside the magnet bore; changes in the signal are caused by the MHE.
Figure 20:
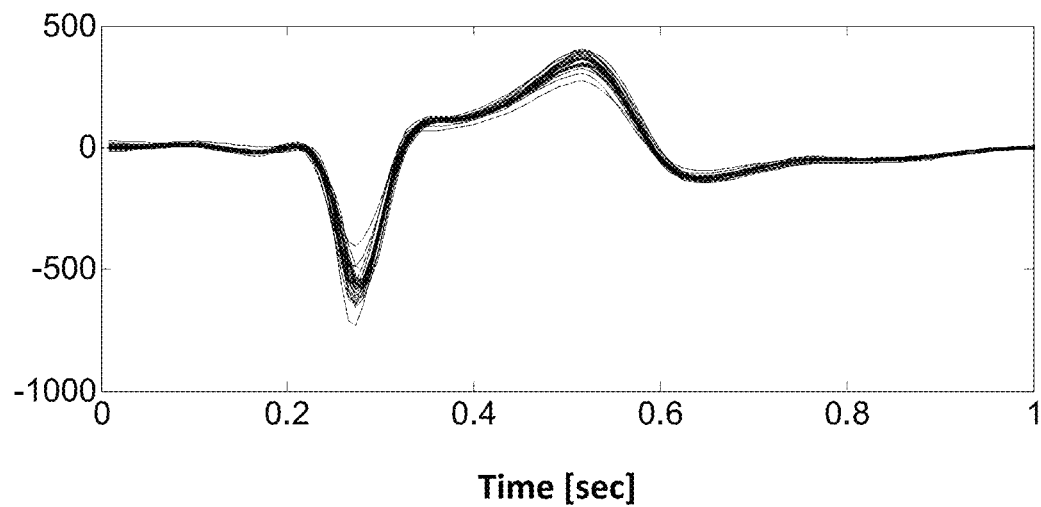
FIG. 20 shows the cardiac complexes that were reconstructed, using the MHE-ECG and the processing steps described in Section IV, "Filtering GMF and MHE Using Signal Reconstruction."
Figure 21:
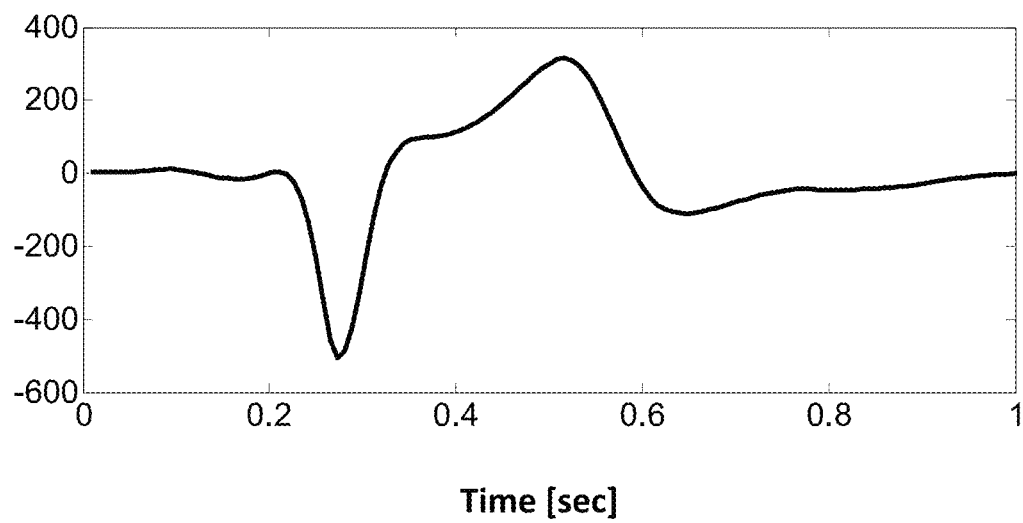
FIG. 21 is an average reconstructed ECG complex.
Figure 22:
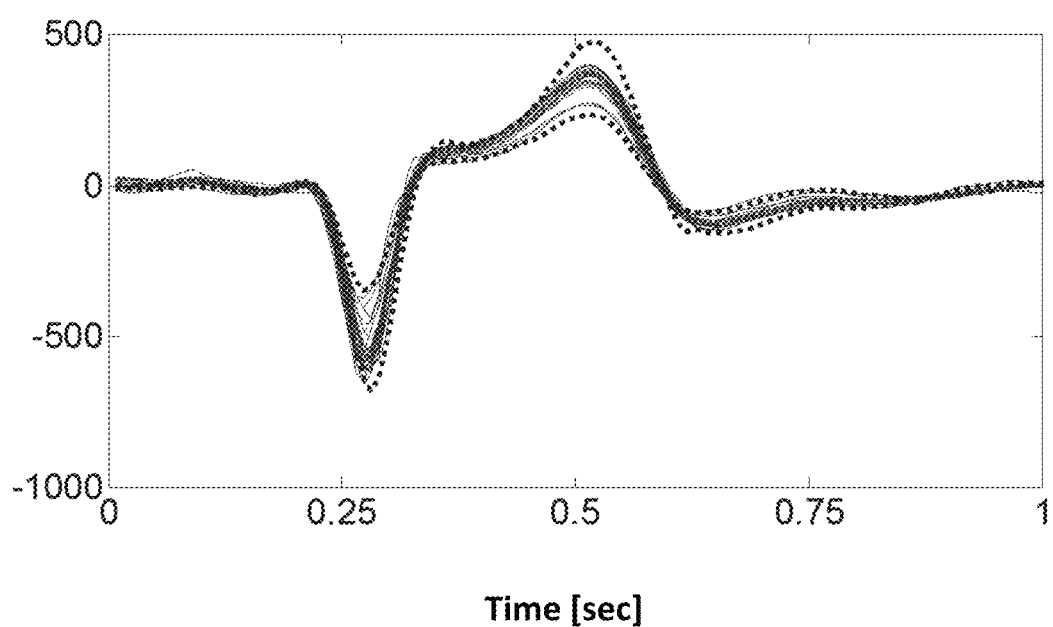
FIG. 22 shows reconstructed ECG complexes (solid lines) superimposed on the range of variations in measured ECG complexes (dashed lines).

FIGS. 18-22 illustrate the processing steps described above. FIG. 18 shows an example of a clean, diagnostic ECG signal (Lead II) recorded outside the magnet bore. FIG. 19 shows the ECG signal in the same lead after the subject was moved inside the magnet bore; changes in the signal are caused by the MHE. FIG. 20 shows the cardiac complexes that were reconstructed, using the MHE-ECG and the processing steps described above. FIG. 21 shows an average reconstructed ECG complex. To compare measured and reconstructed ECG complexes, FIG. 22 shows reconstructed ECG complexes (solid lines) superimposed on the range of variations in measured ECG complexes (dashed lines).

The magnitude of MHE may change due to changes in blood pressure, arterial pressure wave, blood volume, or blood flow. To track changes in these parameters, the system of the present invention uses one or more measurements selected from the MR-based measurements of blood flow, arterial pressure waves and/or blood volume, intra-arterial blood pressure, intra-cardiac blood pressure, venous blood pressure, noninvasively measured blood pressure, arterial and/or intra-cardiac pressure waves measured by photoplethysmography, plethysmography, electrical impedance, pulse oximetry, accelerometry, acoustic waves, ultrasound, infrared, and other optical, mechanical, and electrical signals obtained from an individual's body.

If significant changes in these signals are detected, the transfer matrix $X^+$ is further adjusted, using one or more of the following methods:

a. The patient is moved out of the magnet bore, and a clean (free of MHE), diagnostic ECG is recorded; a new transfer matrix $X^+$ is obtained as described above in section C.

b. The patient remains inside the magnet bore of the MR scanner while the transfer matrix $X^+$ is adjusted using statistical relationships between the changes in blood pressure/flow and MHE. The statistical relationships are obtained from an individual subject's data and/or a group (population) of subjects.

The reconstruction process described above may lead to inaccurate results if the shape of the ECG waveforms deviates from the dominant waveforms, which have been used for computing the transfer matrix $X^+$. Because the dominant ECG waveform in most subjects originates from the sinus node (i.e., sinus beats), the transfer matrix $X^+$ is based on the sinus beats in most subjects. This transfer matrix may not be accurate for reconstructing ectopic beats (e.g., premature atrial complexes and premature ventricular complexes). The system of the present invention allows users to display and compare both unreconstructed and reconstructed signals as they are received. It also allows viewing and comparing newly received data with templates (waveforms, patterns) obtained from multiple, averaged, or median cardiac beats/complexes (e.g., sinus beats, premature atrial complexes, premature ventricular complexes).

Optimized Wireless Data Transmission

This invention provides a novel and efficient way to obviate the limits of the data-transmission rate (speed) of wireless communication, as well as its inherent vulnerability to transmission losses, delays, and complete interruptions, which create significant technical difficulties for the development of multichannel, wireless monitoring systems. It provides fast and reliable data transmission for multiple data channels in real time, using the following improvements:

I. Parallel Transmission of Multiple Channels and/or Groups of Channels Using Several Wireless Transmitters The key elements of this invention include:
a. Utilizing a modular system architecture with the same or similar data-acquisition and processing modules and a wireless transmitter/receiver on each module (or associated with each module);
b. Distributing wireless communication between the wireless transmitter/receiver associated with different modules (instead of a single transmitter/receiver, which is traditionally used in wireless systems as a wireless alternative to a cable transmission); and
c. Synchronizing the modules by passing synchronization signals (i.e., time markers) to one (or more) data channels of some (or all) modules.

Data Synchronization

Data received by different modules can be synchronized by time markers (stamps), which include short, discrete pulses or continuous waveforms (e.g., sinusoidal waves with a constant frequency). The time markers can be generated by one module and transmitted to other modules; they can be also generated by a data-synchronization module or a motherboard and transmitted to all modules. The time markers are recorded by each module into a separate data-synchronization channel and transmitted wirelessly along with other data channels to the data-receiving station. The software on the receiving station (e.g., desktop computer, laptop, smart phone) utilizes the time markers to synchronize the data received from different modules. The synchronization is achieved by time-aligning the time markers, as well as simultaneously acquired data channels received from all modules.

II. Wireless Transmission Using Multiple Transmitters that Operate in Different Frequencies (Frequency Ranges) to Prevent Transmission Loss/Failure A medical device of this invention improves the reliability of wireless transmission (which may become unreliable in the presence of EMI, electromagnetic shields, or changing distance and position of the transmitter relative to a receiver). Distribution of wireless transmission into several independent data streams can provide backup for potential failures in some of the wireless transmission links.

Figure 1:
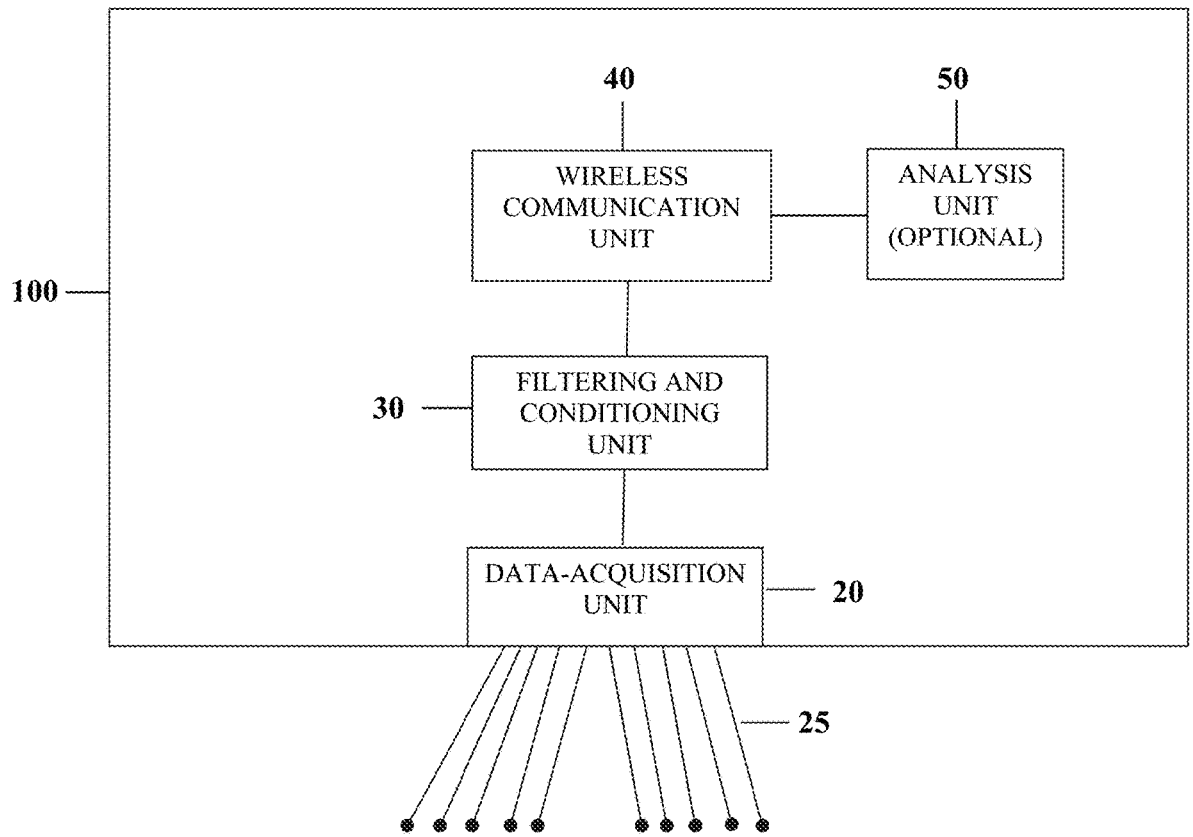
FIG. 1 is a block diagram of an embodiment of the system architecture that includes a data-acquisition module (unit), a wireless communication (transmission) module, a filtering and conditioning module, and an optional analysis module. Note that all these modules are integrated into a single compact, mobile unit.

FIG. 1 is a block diagram of a preferred embodiment of a medical device 100 of this invention. The device consists of a data-acquisition unit 20 (herein, the terms unit, module, circuitry, part, and section are used interchangeably and may refer to electronic hardware, firmware, and software) which may have several cables with electrodes 25 for attachment to a subject (not shown) to receive ECG or other physiological signals in real time; a filtering and conditioning module 30; a wireless communication unit 40 (with optional data synchronization unit/circuitry/firmware); and an optional analysis unit 50. The acquisition unit receives physiological signals through the electrodes 25 that are connected to a subject. As used herein, subject means a human or an animal.

Block diagrams of several configurations of the data-acquisition and filtering parts of a medical device of this invention are shown in FIGS. 6-11.

Figure 6:
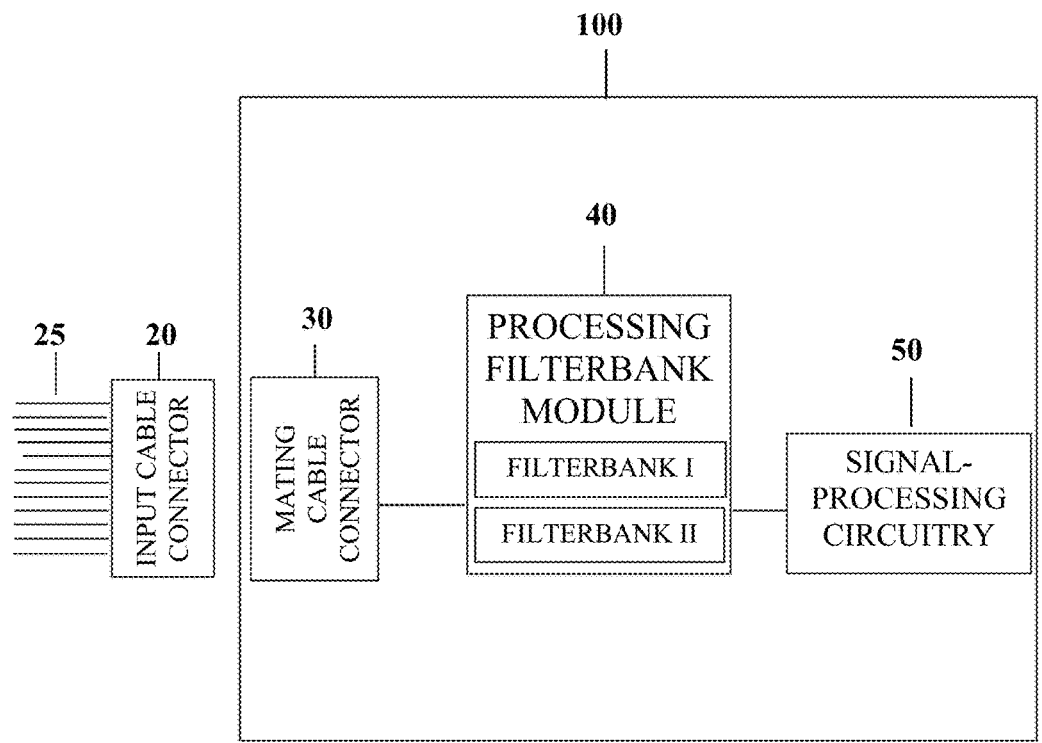
FIG. 6 is a block diagram of the system configuration with two switchable filterbanks. The filterbanks are selected using a mechanical, electronic, or programmable switch.

In FIG. 6, physiological signals are received through cables/electrodes 25, which are attached to a subject on one side and an input cable connector 20 on another side. The input cable connector attaches to a medical device of this invention through a mating cable connector 30, which transmits the acquired signals to a processing filterbank module 40. The filterbank module 40 consists of two or more switchable filterbanks (Filterbank I and II), which are selected using a mechanical, electronic, or programmable switch. The signals filtered through the selected filterbank are passed to the signal-processing circuitry 50 for further processing and analysis.

Figure 7:
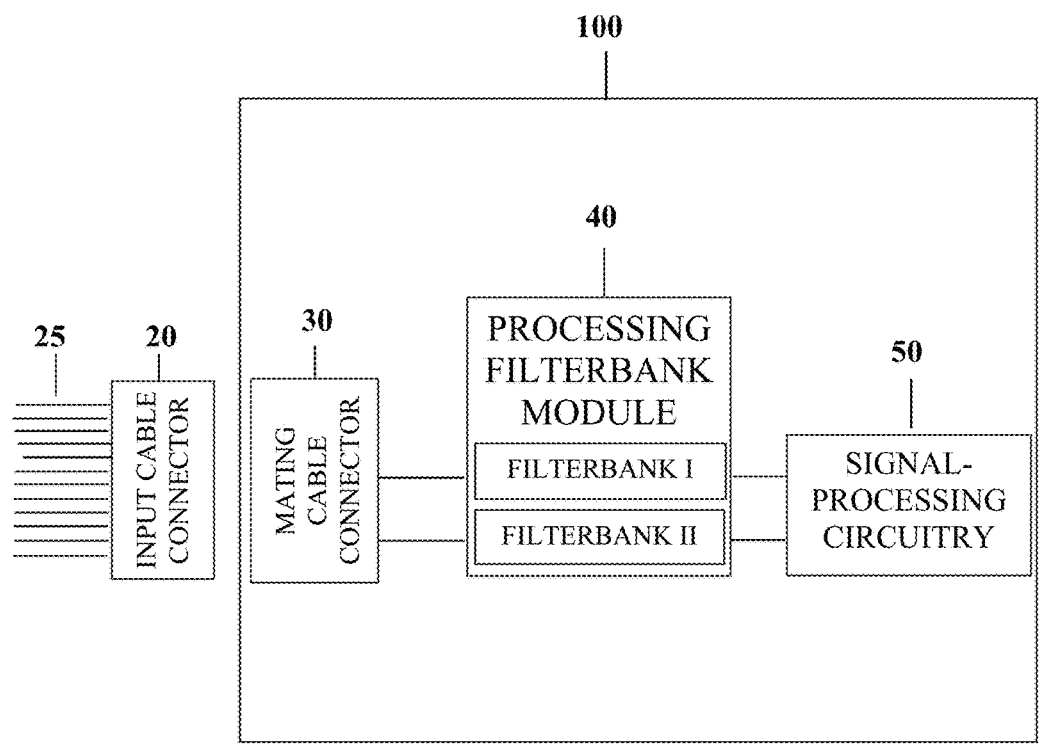
FIG. 7 is a block diagram of the system configuration with two parallel filterbanks; all data channels are filtered through two different filterbanks. This configuration doubles the number of data channels, because the two filterbanks produce two parallel data streams that are passed to the signal-processing circuitry 50.

FIG. 7 is a block diagram of the system configuration, which is similar to that in FIG. 6. However, in this configuration the filterbanks in module 40 are configured to provide parallel filtering, which doubles the number of data channels that are passed to the signal-processing circuitry 50. The two parallel data streams are necessary for determining the transfer function between the two data streams and reconstruction of diagnostic-quality signals in the presence of GMF interference and MHE, as described in the Summary of the Invention (Section II, "Filtering GMF Using Parallel Filterbanks").

Figure 8:
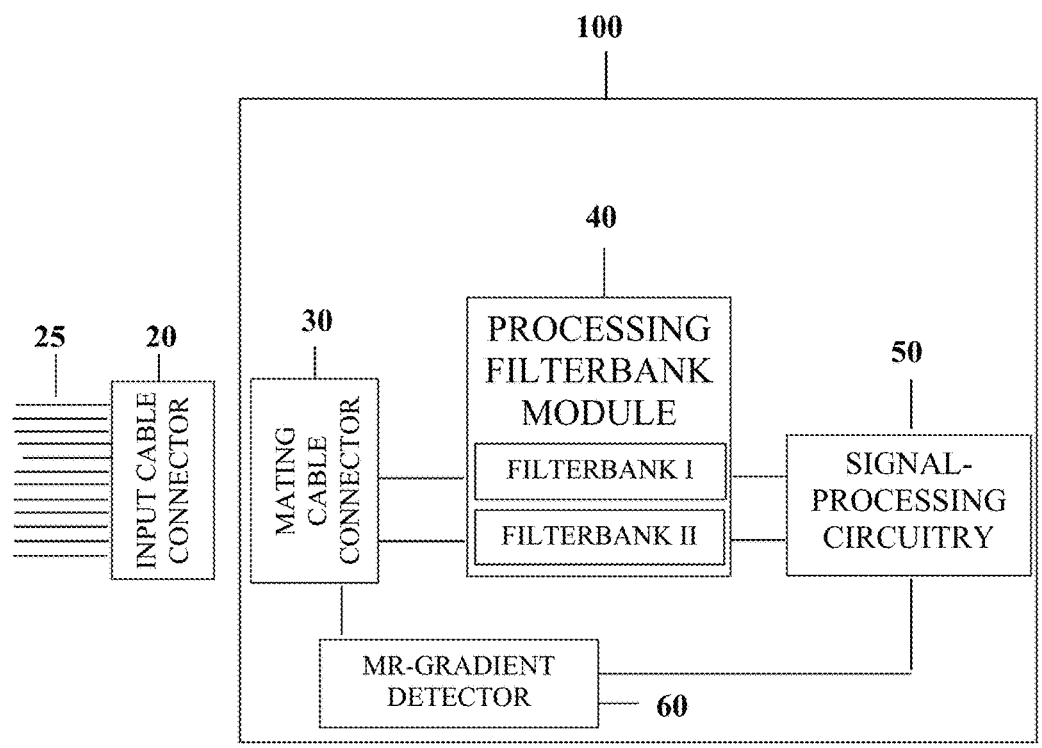
FIG. 8 is a block diagram of the system configuration with an MR-gradient detector 60, which receives the signals from the mating cable connector 30 and passes the GMF-detection information to the signal-processing circuitry 50.

FIG. 8 shows a block diagram of system configuration, which is similar to that in FIG. 7 but also includes the MR-gradient detector 60, which receives the signals from the mating cable connector 30 and passes the GMF-detection information (i.e., about the beginning and end of GMF events) to signal-processing circuitry 50.

Figure 9:
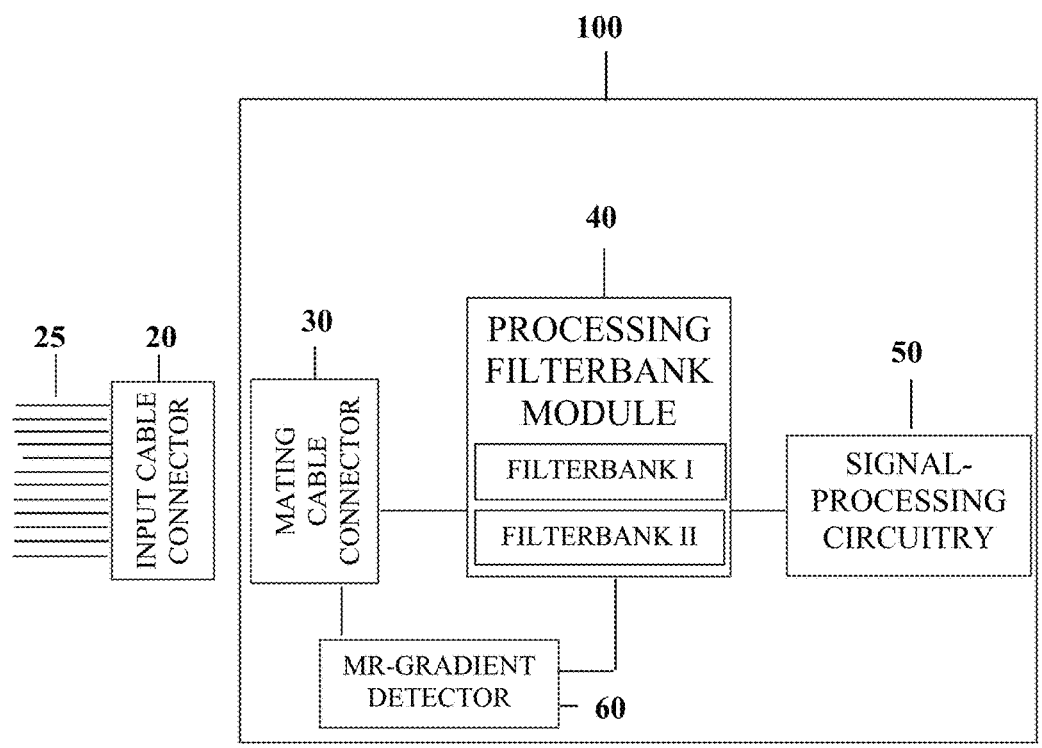
FIG. 9 is a block diagram of the system configuration with an MR-gradient detector 60, which receives the signals from the mating cable connector 30 and passes the GMF-detection information to the processing filterbank module 40.

FIG. 9 is a block diagram of the system configuration, in which an MR-gradient (GMF) detector 60 passes the GMF-detection information to the processing filterbank module 40. This configuration allows programmable switching of the filterbanks in module 40 at the time points of GMF detection based on the information received from the GMF detector 60. The programmable switching is preferably implemented using digital signal processing, which provides very short switching time.

Figure 10:
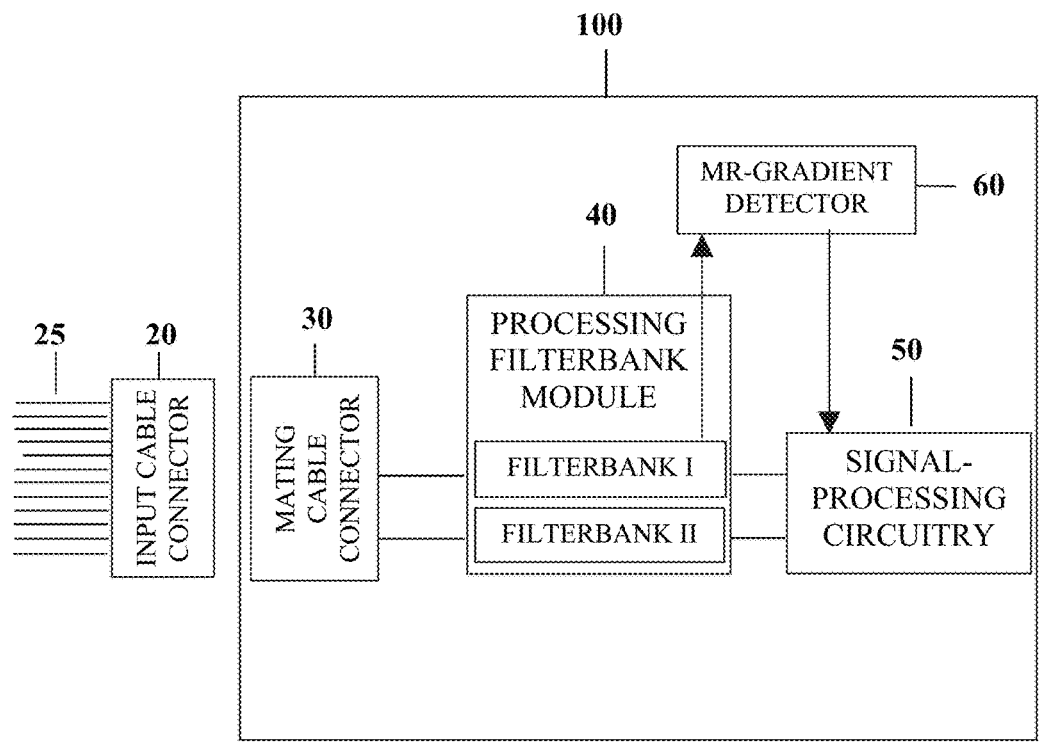
FIG. 10 is a block diagram of the system configuration with an MR-gradient detector 60, which receives the signals from the Filterbank I and passes the GMF-detection information to the signal-processing circuitry 50.

When the level of GMF is very high, a medical device of this invention uses an MR-gradient detector 60, which is connected to a processing filterbank module 40, as shown in FIG. 10, to prevent amplifier saturation. To further enhance filtering of powerful GMF levels, a pre-processing filterbank module 70 is incorporated as shown in FIG. 11. Module 70 includes two or more filterbanks; Filterbank P1 provides reduction of a signal's magnitude, whereas Filterbank P0 passes signals through without any changes. The procedures for reducing signal magnitude in Filterbank P1 include voltage division and bitwise operations, as described in the Summary of the Invention (Section III, "Filtering GMF Using Time-Domain GMF Features").

Figure 23:
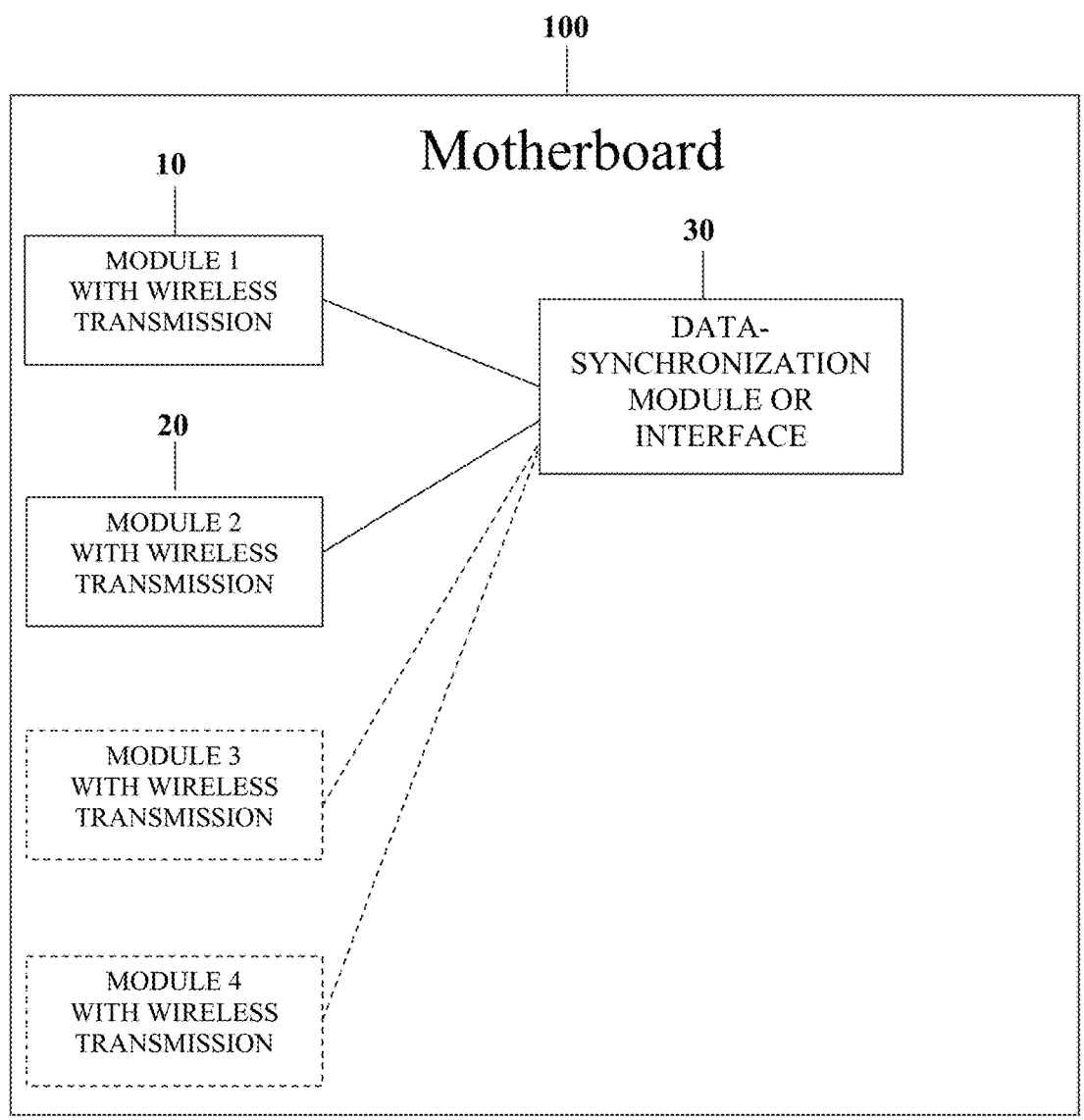
FIG. 23 is a block diagram of a system's embodiment with two data-acquisition and/or processing modules, as well as a data-synchronization unit/interface.
Figure 24:
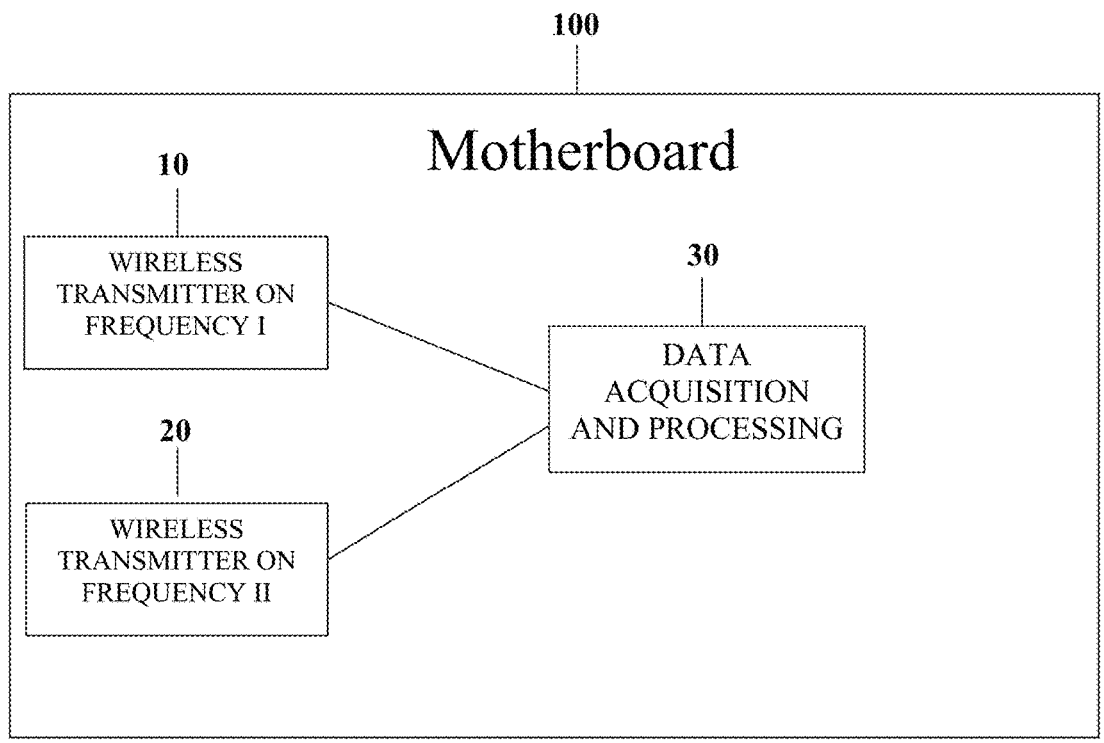
FIG. 24 is a block diagram of a system's embodiment with two radio transmitters, which transmit data concurrently using two different frequency ranges to prevent data loss in case one of the transmission frequencies fails.

Configuration of a wireless communication unit of a medical device of this invention, as well as data-synchronization unit/interface, are shown in FIGS. 23 and 24. In FIG. 24, each data-acquisition module (module 10, module 20, etc.) has an associated wireless transmitter. Each module provides data acquisition and/or processing for some of the data channels, and has a wireless transmitter associated with it (e.g., Bluetooth, WiFi, or Zigbee). For example, Module #1 provides multi-channel acquisition of ECG data, whereas Module #2 provides multi-channel acquisition of blood pressure and pulse-oximetry data. For systems with a large number of data channels (e.g., cardiac electrophysiology, EMG, or EEG monitoring systems), the number of modules can be further increased, as required.

The wireless modules serve two purposes:
a. An interface for programming data-acquisition parameters for each module (sampling rate, resolution, number of channels, duration of data acquisition, and data transmission mode [real-time transmission or recording to each module's memory card]), and
b. Real-time data transmission to a receiving station.

In this configuration, each module acquires and transmits data via its associated wireless transmitter, producing parallel data streams, which are aggregated, synchronized, processed, and displayed at the receiving station (not shown). The modules are synchronized using a periodic impulse and/or frequency signal (with known frequency characteristics, e.g., a 1 kHz sine wave), which serve as time markers. These time markers are generated by Module #1 or a separate data-synchronization module/interface 30 and recorded to the reference-data channel of all modules, along with simultaneously acquired data channels. Because the time markers are generated and recorded by each module simultaneously with other data channels, the receiving station synchronizes the data by time aligning the corresponding time markers (as well as simultaneously acquired data channels) in all modules.

FIG. 23 is a block diagram of a system's embodiment with two radio transmitters, which transmit data using two different frequency ranges to prevent data loss in case one of the transmission frequencies fails. In a preferred embodiment of a medical device of this invention, the same data are transmitted independently and concurrently by two (or more) transmitters using two different transmission frequencies (e.g., 2.4 and 5.2 GHz); this parallel transmission ensures that the data will be received by one or more receivers utilizing one of the transmission frequencies, even if the second transmission link fails (FIG. 24).

In another configuration of a medical device of this invention, wireless transmission includes intelligent, "on-demand" re-routing of data from failed wireless links (transmitters) to working ones. Examples of such wireless transmitters include: (i) transmitters of the same type (e.g., two Bluetooth transmitters), (ii) transmitters of different types (e.g., Bluetooth and Wi-Fi), and (iii) transmitters of the same type but with different transmission frequencies (e.g., Wi-Fi operating on 2.4 and 5.2 GHz).

Wireless transmitters of the same type often share the same transmission frequency range. For example, Bluetooth transmitters use ~2.4 GHz frequency range with adaptive frequency hopping, which may create interference between several Bluetooth radios transmitting data at the same time. To obviate this problem, the Bluetooth transmission protocols in one configuration of a medical device of this invention are adapted to the presence of other Bluetooth transmitters by dividing the transmission spectrum, thus avoiding interference between them.

Figure 25:
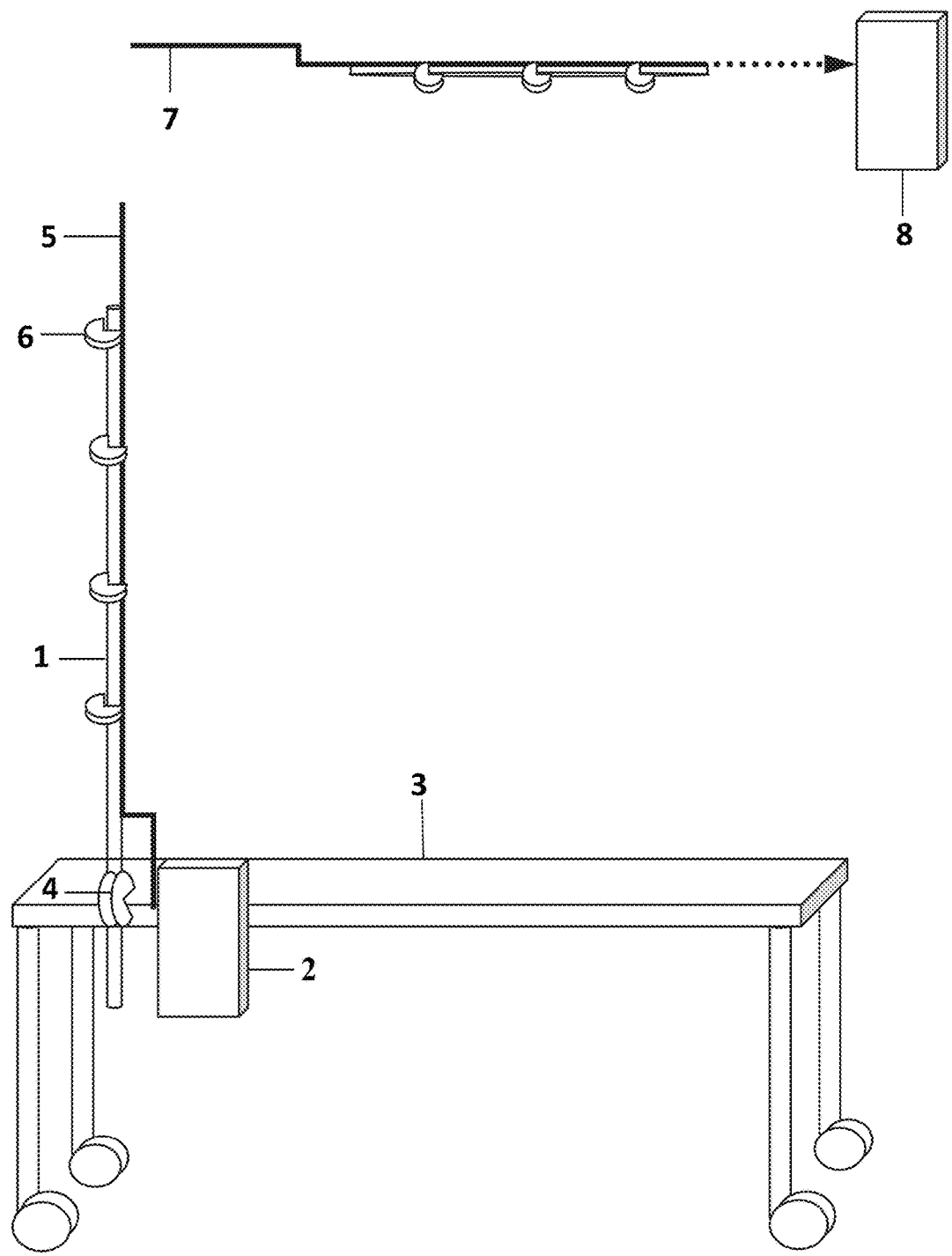
FIG. 25 shows a wireless antenna mount 1; a data-acquisition and wireless-transmission unit of this invention 2 is attached to a mobile patient table 3 using a c-lamp 4. The wireless antenna 5 is attached to the antenna mount using a series of mounting hooks 6, c-clamps, or Velcro straps. The unit 2 transmits data wirelessly, using the transmitting antenna 5, to a receiving wireless antenna 7, which is mounted on the ceiling to provide substantially unimpeded wireless transmission for various locations of the patient table. The receiving antenna is connected to a wireless receiver unit 8, which can be located in the same room or in a different room. The wireless receiver unit can also include processing, analysis, and display of the received physiological signals.

FIG. 25 shows one embodiment of this invention in which a wireless antenna mount 1 and a data-acquisition and wireless-communication (transmission) module 2 are attached to a mobile patient table 3 using a c-clamp 4 or other mounting device. A wireless antenna 5 connected to module 2 is attached to the mounting pole 1 using a series of hooks 6, c-clamps, or Velcro straps. The mounting poles that can be used for mounting a wireless antenna include a lighting holder arm, a lighting stand, and other types of stands.

Because the first antenna 5 stays with the patient table as the table (and the patient) is being moved during a procedure or between different procedure rooms, it provides uninterrupted wireless communication during patient (and patient-table) movement. The second antenna 7 is mounted on the ceiling or on the wall; it extends at least six feet above the floor to provide unimpeded communication with the first antenna 5 during table movement as well as during the movement of medical personnel and equipment around the table (bed). Thus, in this embodiment, wireless communication between the two antennas is carried out in the space (plane) at least six feet above the floor that is not affected by patient-table, personnel, or equipment movement. The second antenna 7 is connected to the receiving and processing unit/module 8, which is located in the same room (mounted on the ceiling or on the wall) or in another (e.g., adjacent) room.

Figure 26:
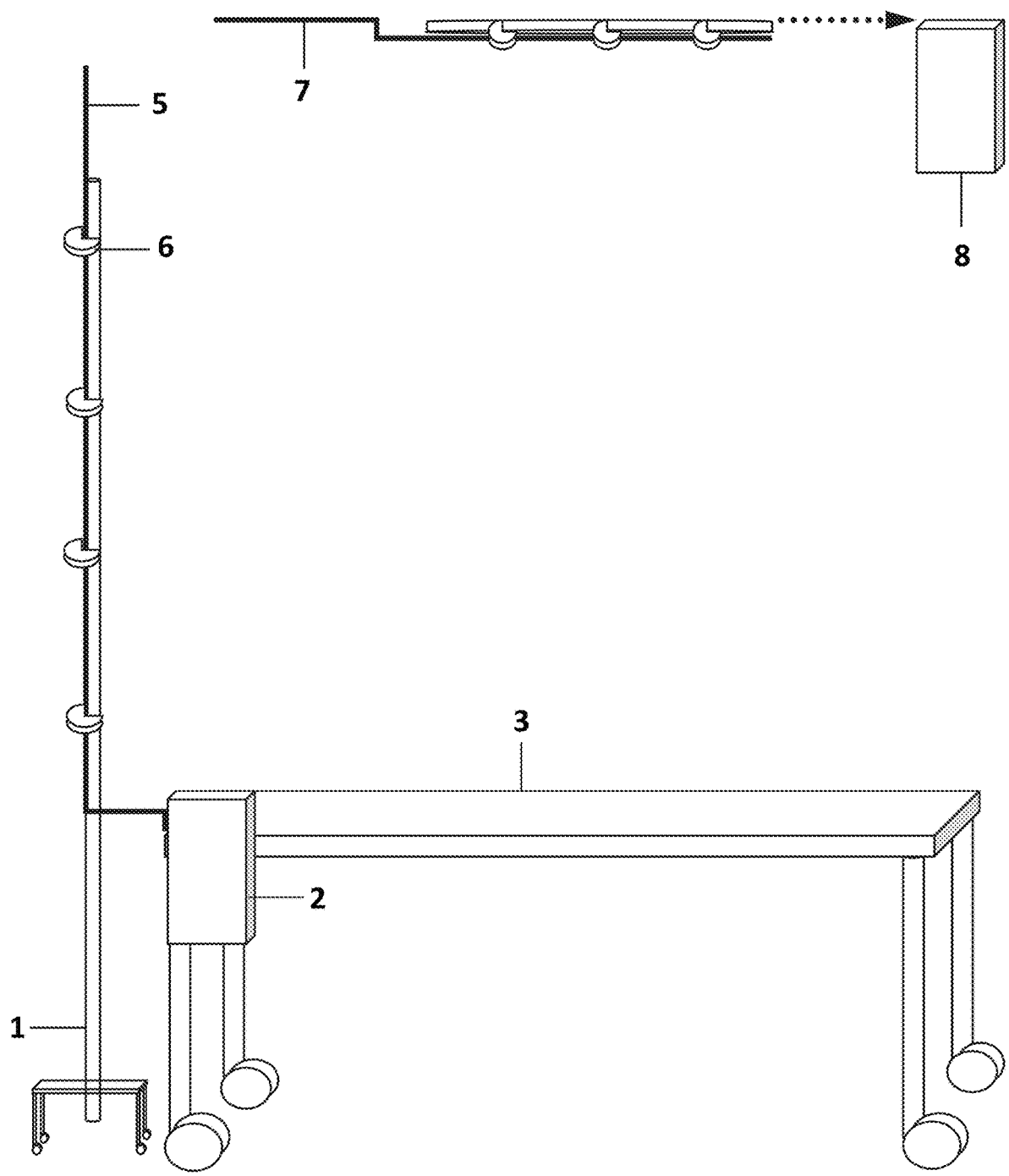
FIG. 26 shows a freestanding wireless antenna mount 1, which has its own stand on wheels. The data-acquisition and wireless-transmission unit (module) of this invention 2 is attached to a patient table 3 using a c-clamp or mounting device (not shown). The wireless antenna 5 is attached to the antenna mount using a series of mounting hooks 6, c-clamps, or Velcro straps. The unit 2 transmits data wirelessly, using the transmitting antenna 5, to a receiving wireless antenna 7, which is mounted on the ceiling to provide substantially unimpeded wireless transmission for various locations of the patient table. The receiving antenna is connected to a wireless receiver unit 8, which can be located in the same room or in a different room. The wireless receiver unit can also include processing, analysis, and display of the received physiological signals.

FIG. 26 shows an embodiment of this invention in which a wireless antenna 5 is mounted on a freestanding mounting pole 1 and is secured using a series of hooks 6, whereas the data-acquisition and wireless-transmission unit 2 is attached to the patient table 3. The receiving antenna 7 is mounted to the ceiling or to the wall to provide uninterrupted communication with the transmitting antenna during various movements of the patient table and medical personnel. The receiving antenna is connected to the wireless receiver and processing unit 8.

Figure 27:
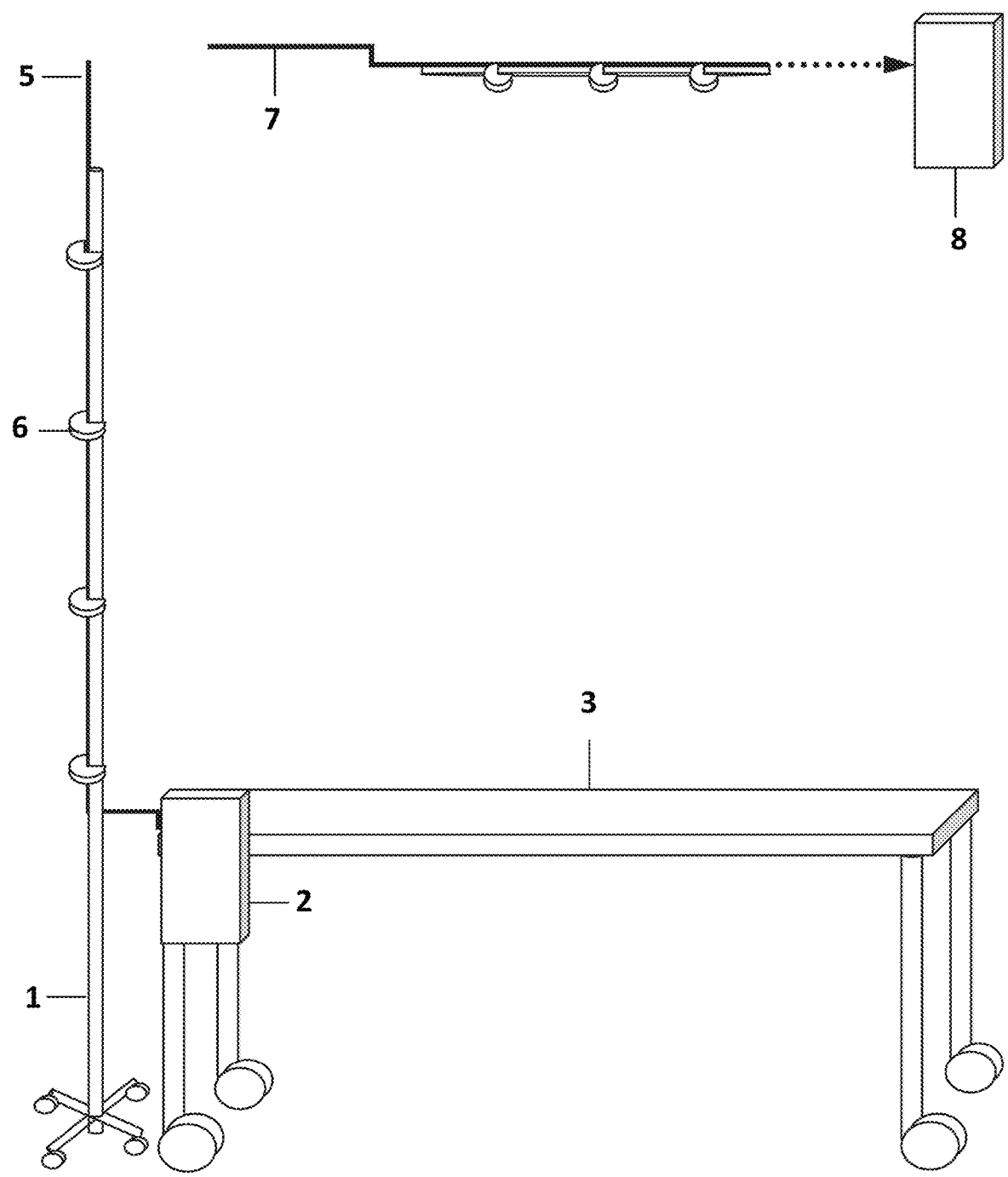
FIG. 27 shows a wireless antenna 5 mounted on an intravenous (IV) infusion pole (mount) 1, which can also be used for hanging IV fluid bags. The data-acquisition and wireless-transmission unit of this invention 2 is attached to a patient table 3 using a c-clamp or mounting device (not shown). The wireless antenna 5 is attached to the antenna mount using a series of mounting hooks 6, c-clamps, or Velcro straps. The unit 2 transmits data wirelessly, using the transmitting antenna 5, to a receiving wireless antenna 7, which is mounted on the ceiling to provide substantially unimpeded wireless transmission for various locations of the patient table. The receiving antenna is connected to a wireless receiver unit 8, which can be located in the same room or in a different room. The wireless receiver unit can also include processing, analysis, and display of the received physiological signals.

FIG. 27 shows an embodiment of this invention in which a wireless antenna 5 is mounted on a freestanding IV infusion pole 1, which may also hold a hanging IV fluid bag, and is secured using a series of hooks 6, whereas the data-collection and transmitting unit 2 is attached to the patient table 3. The receiving antenna 7 is mounted to the ceiling or to the wall to provide uninterrupted communication with the transmitting antenna during various movements of the patient table and medical personnel. The receiving antenna is connected to the wireless receiving and processing unit 8.

In one embodiment, the transmitting antenna extends to at least six feet above the floor to provide substantially unobstructed communication with one or more receiving antennas, which are also positioned at least six feet above the floor.

In one embodiment, the transmitting antenna is located below patient level to provide substantially unobstructed communication with one or more receiving antennas located on the floor surface (below the patient). In one embodiment, the frame of the patient table (bed) serves as a transmitting antenna.

In one embodiment, the transmitting antenna is fed through (mounted inside) a hollow pole, which can be also used for hanging IV fluid bags. In a preferred embodiment, the pole is mounted (connected) to the patient table. The antenna mount is attached to the patient table using, for example, a c-clamp, and stays with the patient table as the patient is moved during different procedures as well as between different procedure rooms.

An important aspect of this invention is adaptive filtering and signal conditioning implemented in a DSP module/unit. The DSP operations are adapted to the properties of EMI and recorded data (physiological signals), using:

a. Adaptive selection (control) of the channel (signal) for EMI detection;
b. Adaptive selection (control) of the detection parameters (e.g., magnitude and duration of the EMI peaks and the time interval between them), as described below;
c. Adaptive selection (control) of the channel (signal) for the detection of cardiac-activity waveforms (e.g., ECG QRS complexes); and
d. Adaptive selection (control) of the detection parameters for cardiac-activity waveforms (e.g., magnitude and duration of the ECG QRS complexes and the time interval between adjacent QRS complexes).

The system of this invention provides means (tools, mechanisms) for the channel selection and control (adaptation) of the DSP operations described above. These control means include one or more of the following tools:

a. User-controlled mechanical or electrical switches, adaptive software and firmware providing user-controlled adaptation parameters described above; and
b. Automatic adaptation of the DSP operations described above using programmable feedback/control software and firmware based on the EMI and cardiac waveform signals in different channels as described below.

Adaptive EMI Filtering

An important aspect of this invention is the selection of the channel for the detection of EMI spikes/peaks/artifacts (herein referred to as the "base-EMI channel"). Similar to the cardiac-activity-waveform tracking described below, the invention relies on the fact that the time of EMI peaks is the same in all channels. Therefore, the time points of occurrence of EMI peaks are determined in the base-EMI channel first. Subsequently, the same time points are used for tracking (and filtering) EMI in other channels.

The base-EMI channel is selected either by user (user-guided selection) or by the system (unguided selection) based on automatically determined EMI signal characteristics, such as the EMI-peak magnitude and/or signal-to-noise ratio (SNR).

When the times of occurrence of EMI peaks have been determined in the base-EMI channel, the EMI filtering is performed in other channels (physiological signals), using:
a. the times of the EMI peaks in the base-EMI channel;
b. the duration of the EMI-filtering time window (i.e., the time interval during which the EMI is removed from all filtered channels), which can be selected either by a user (user-guided selection) or by the system (unguided selection) based on the automatically determined EMI signal properties (characteristics) in various channels, such as the EMI-peak magnitude and duration; and
c. the duration of the cardiac-activity-waveform-protection time window (herein referred to as the pivot window), during which EMI filtering is not performed in order to protect essential features of the cardiac-activity waveforms (e.g., ECG P, QRS, ST, and T waves) from filtering.

The EMI-detection and -filtering parameters, including the magnitude and derivative thresholds for detecting EMI peaks, duration of the EMI-filtering window, and the pivot window, are selected either by a user (user-guided selection) or by the system (unguided selection) based on the EMI signal properties, such as the magnitude and duration of EMI peaks and the time interval between them.

Tracking Cardiac-Activity Waveforms

The filtering and conditioning module identifies and tracks various forms of cardiovascular activity (e.g., ECG activity and its P, QRS, and T waves; ABP waveforms; and pulse-oximetry waveforms). The DSP module also identifies and tracks EMI, e.g., GMF-generated spikes (peaks), whose frequency spectrum may overlap with the spectrum of QRS complexes. This overlap makes discrimination between the ECG QRS complexes (or other waveforms of cardiovascular activity) and GMF-generated EMI spikes technically challenging.

The filtering and conditioning module resolves this technical challenge by enabling selection of the channel (herein referred to as the "base channel") that is used for detection of cardiac-activity waveforms (e.g., ECG QRS complexes) and calculation of associated physiological parameters (e.g., heart rate or beat-to-beat intervals, duration of the QRS complexes and/or QT intervals). The base channel is selected either by a user (user-guided selection) or by the system (unguided selection) based on automatically determined cardiac-activity signal (waveform) characteristics, such as the magnitude of ECG R waves and/or their SNR (where noise includes ambient noise and GMF-generated EMI).

The invention relies on the fact that the time of a specific type of cardiac activity (e.g., ECG activity and its QRS complex) is the same in all channels (i.e., in all ECG leads). Therefore, it is possible to select a base channel in which cardiac activity (e.g., QRS complexes of high magnitude and high SNR) are readily identifiable and EMI is relatively small. Thereafter, this base channel is used for detection and tracking of cardiac activity (e.g., QRS complexes) and calculation of heart rate and other physiological parameters (beat-to-beat intervals, ST-segment amplitude, QT intervals, QRS duration, and T-wave amplitude). Once the time points of occurrence of the ECG QRS complexes have been determined in the base channel, the same time points are used for detecting QRS complexes in other channels. Some other examples of physiological signals that can also be detected and tracked using the base channel include ECG P waves and T waves, ABP waveforms, pulse-oximetry waveforms, and other cardiovascular parameters.

The cardiac-waveform (e.g., ECG QRS complexes) detection parameters, including the magnitude and derivative thresholds, the QRS duration, and the time interval between adjacent QRS complexes, are selected either by a user (user-guided selection) or by the system (unguided selection) based on the properties of the cardiac waveforms, such as the magnitude and duration of ECG QRS complexes or other ECG waves, as well as their SNR. Averaging and other forms of low-pass filtering are used to improve the SNR. Parameter selection may also include the properties of cardiac activity (e.g., the magnitude and duration of ECG QRS complexes or other ECG waves, the time interval between adjacent QRS complexes, and their SNR).

The filtering and conditioning module is implemented in a microcontroller (e.g., Texas Instruments, MSP-430), a microprocessor (e.g., Texas Instruments KEYSTONE, ARM CORTEX, C6000, Intel CORE i7 or ATOM, or an ATMEL ARM CORTEX processor), an FPGA (e.g., Xilinx SPARTAN FPGA, Xilinx VIRTEX FPGA, or Altera Cyclone FPGA), a CPLD, a system-on-chip, or a general-purpose personal computer.

Figure 28:
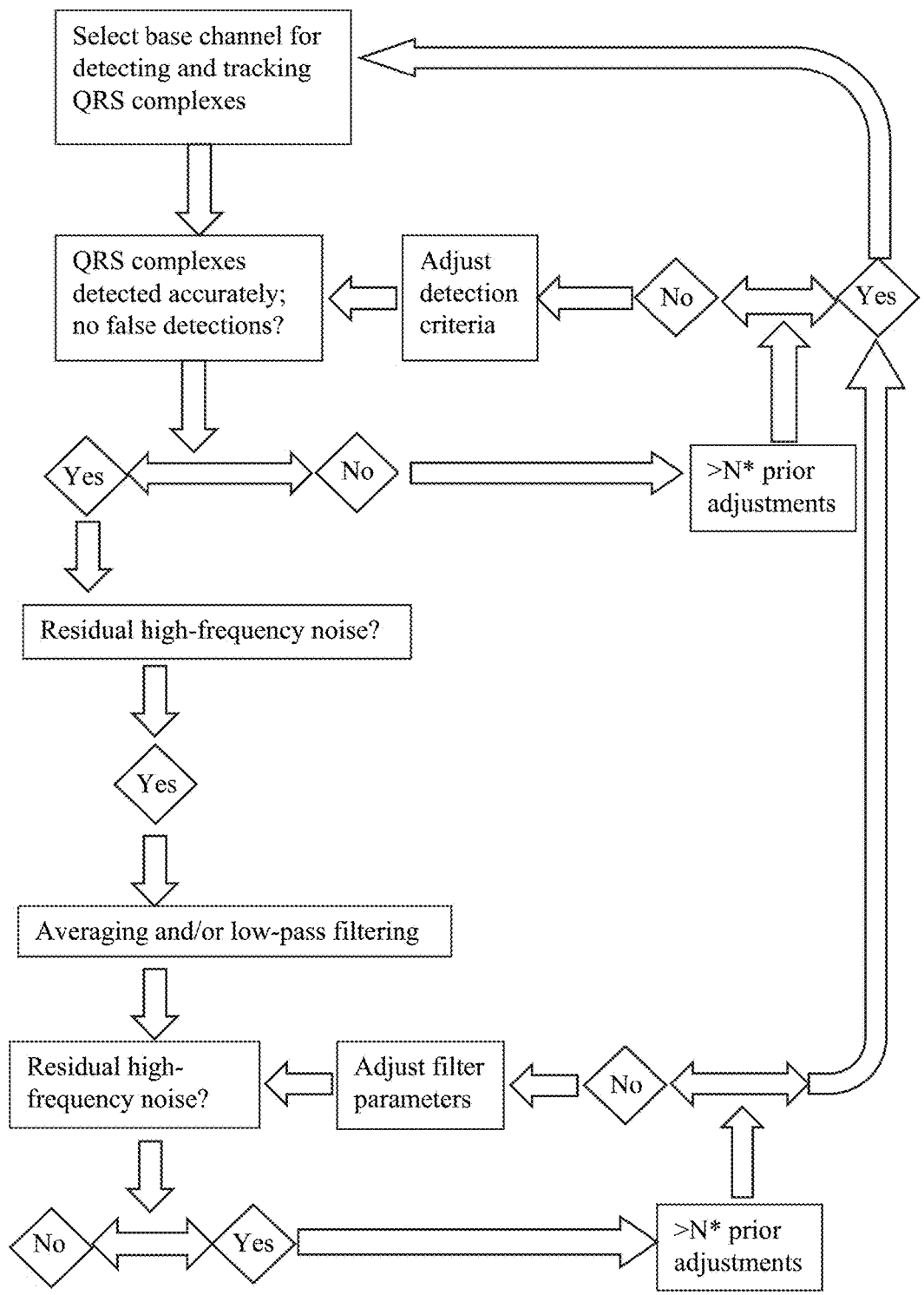
FIG. 28 is a flowchart of an adaptive DSP module performing tracking of cardiac activity (ECG QRS complexes).
Figure 29:
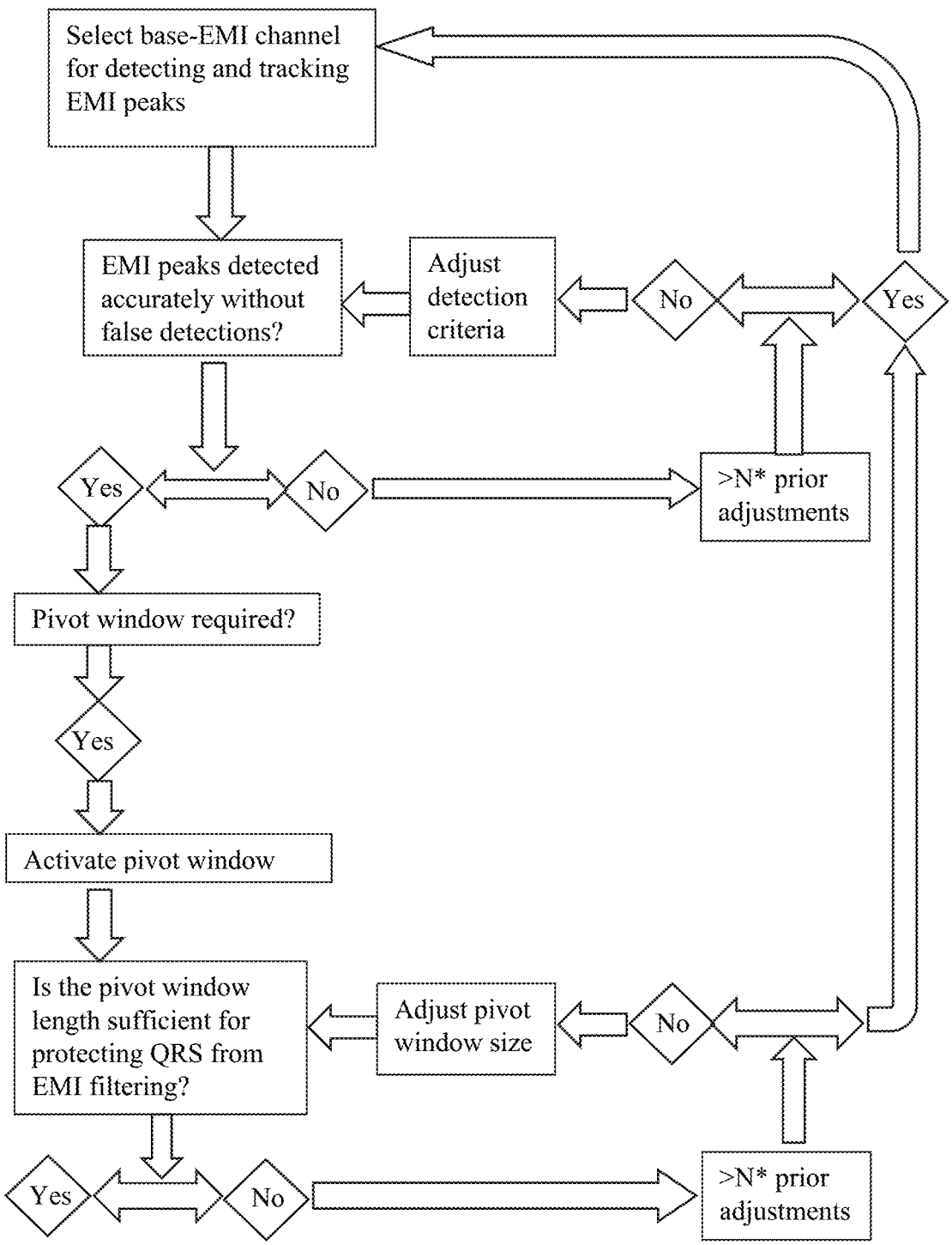
FIG. 29 is a flowchart of an adaptive DSP module performing EMI filtering.
Figure 30:
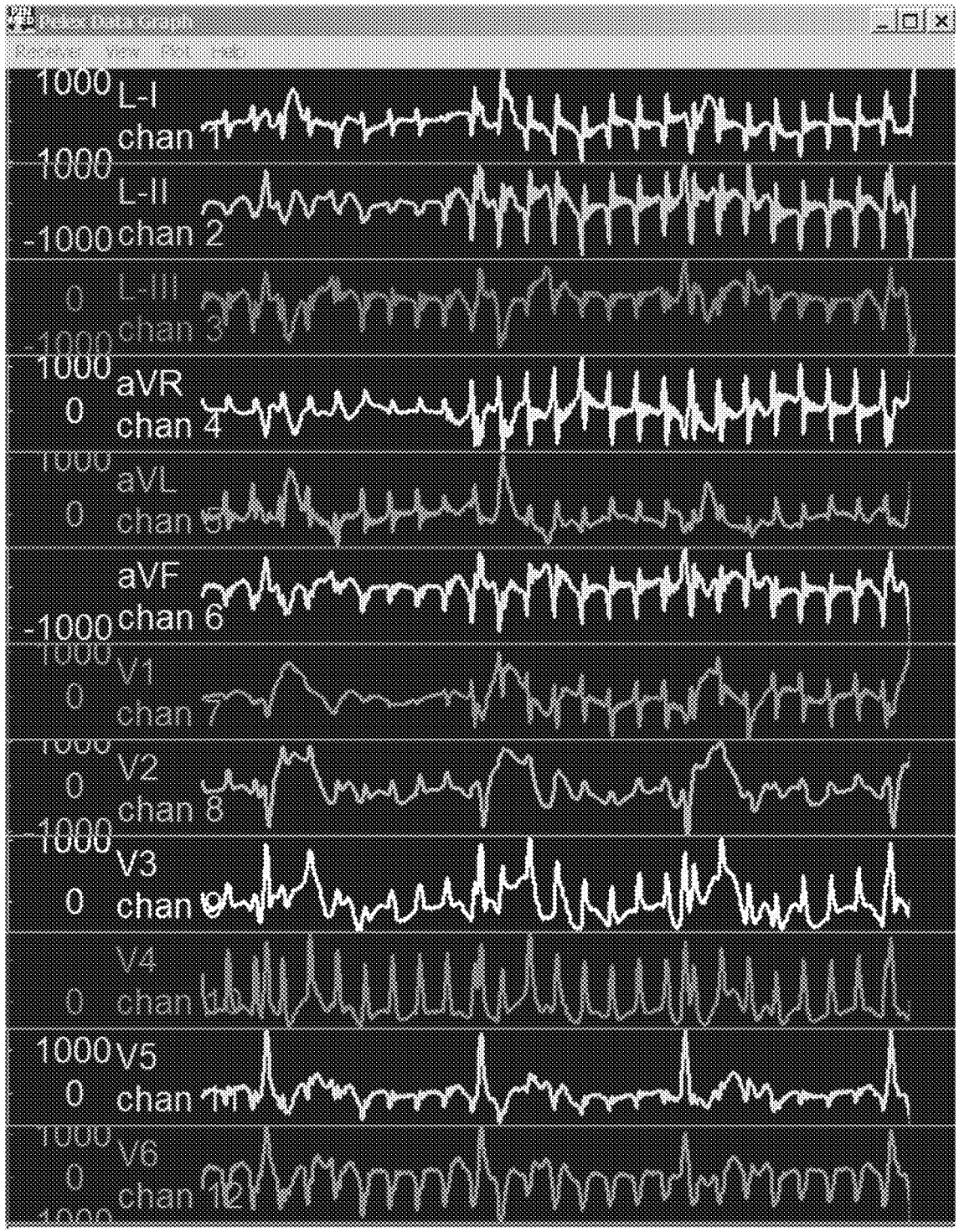
FIG. 30 shows an example of 12-lead ECG during real-time CMR scanning (2-dimensional steady-state free precession [SSFP] pulse sequence) with ~4 ms TR and ~2 ms TE. The EMI filtering is OFF. Note that the scanner produced GMF-generated high-frequency EMI spikes, which completely obscure ECG activity in most ECG leads.
Figure 31:
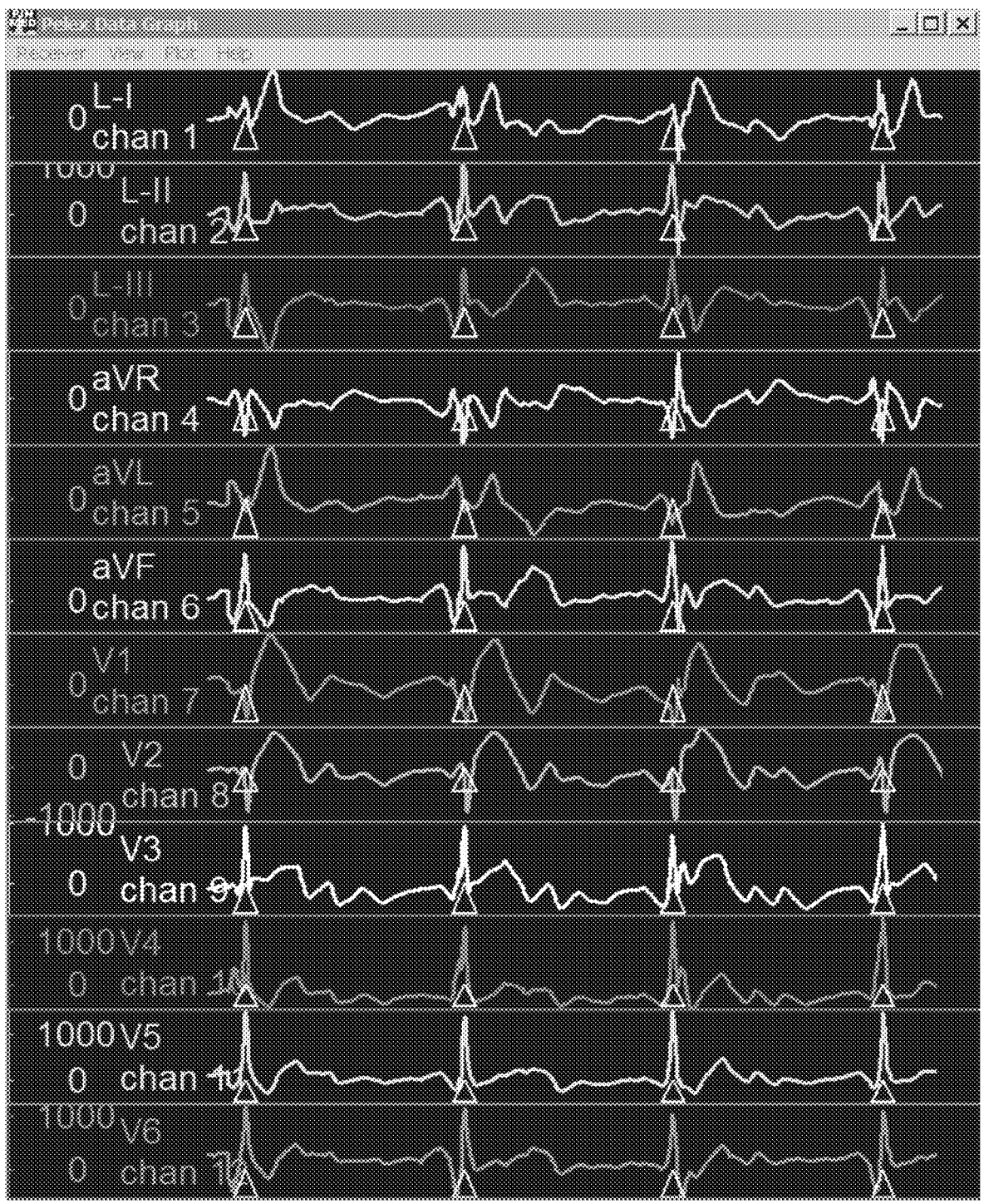
FIG. 31 shows the 12-lead ECG from FIG. 30 with the EMI filtering ON. The EMI filtering was performed using the following parameters: base EMI channel=10, EMI-peak amplitude: 0.5 of the total signal range, EMI-peak separation: 60, EMI-clearance window around the EMI peak: from −60 to 50 ms, base channel=10, QRS peak amplitude: 0.8 of the total range, peak-to-peak separation: 100 ms, pivot window around the QRS complex: from −30 to 40 ms. Note that the EMI spikes were successfully filtered from the ECG signals with minimal changes in the QRS complexes (which are marked by triangles).

FIG. 28 shows a flowchart of one embodiment of the adaptive DSP module performing tracking of cardiac activity (ECG QRS complexes). FIG. 29 shows a flowchart of one embodiment of the adaptive DSP module performing EMI filtering. FIG. 30 shows an example of 12-lead ECG recorded during cardiovascular MRI, using a 2D SSFP sequence with ultra-short duty cycle (TR ~4 ms, TE ~2 ms). Note that high-frequency EMI spikes completely obscure ECG QRS complexes when the EMI filtering is OFF. FIG. 31 shows the 12-lead ECG from FIG. 30 when the EMI filtering is ON. Note that the EMI spikes were filtered from the ECG signals with minimal distortion of the QRS complexes.

Example 1

CMR

Interventional MRI (I-MRI) allows physicians to perform minimally invasive and catheter-based diagnostic procedures, providing high-quality images of internal organs, without exposure to harmful ionizing radiation. I-MRI requires telemetry monitoring of patients' vital signs; however, existing telemetry monitors have electromagnetic compatibility issues: MRI equipment is affected by EMI from telemetry systems, and telemetry data are degraded by the EMI generated by the MR scanner. Commercial applications of the technology are expected to be in all areas of I-MRI. Because I-MRI enables physicians to perform minimally invasive procedures, eliminating the need for more invasive and traumatic procedures, its role in diagnostic evaluation is expected to grow rapidly.

As the field and applications of I-MRI continue to grow and diversify, the need for wireless-telemetry monitoring of various physiological signals (multi-channel ECG, blood pressure, and pulse oximetry) is expected to follow. Thus it is important to develop a platform technology that is not limited to a small number of signals/channels, but has a sufficient number of channels and functions to be utilized for various future applications.

One particularly important emerging area of I-MRI is CMR, which requires high-fidelity, real-time monitoring of multi-channel ECG for timely detection of life-threatening arrhythmias (which can be induced by cardiac catheterization) or the first signs of ischemic changes in the ST-segment. The latter is essential for the monitoring of patients with known or suspected coronary artery disease undergoing an exercise stress CMR test.

However, currently available ECG telemetry systems are limited to a few channels of non-diagnostic-quality ECG, which cannot provide accurate tracking of the ST segment's amplitude and thus do not allow accurate and timely detection of potentially life-threatening ischemic events. Moreover, several telemetry units would be required for wireless monitoring of ECG, oxygen saturation, and ABP, creating logistical difficulties for the medical personnel performing I-MRI procedures.

Example systems of this invention may use wireless and/or non-wireless (e.g., USB cable) connection for transferring the data to a PC without delay (which is inherent for the wireless transmission at 2.4 or 5.2 GHz). In some preferred embodiments, the system utilizes the data acquisition and processing circuitry disclosed on FIG. 12 and FIG. 13 to minimize the EMI generated by the GMFs of an MRI scanner.

In this hypothetical example, an interventional CMR procedure is performed in a human subject, using a medical device of this invention. First, 10 ECG cables (for acquiring 12-lead ECG), two cables for monitoring blood pressure using fluid-filled pressure cables, a cable for monitoring blood pressure noninvasively, and a fiber-optic cable for monitoring pulse wave (pulse oximetry) are attached to the subject. The first set of signals may be acquired outside the magnet bore providing an MHE-free reference data. The second set of signals may be acquired after the patient is moved inside the magnet bore but before scanning begins. This set of signals contains MHE but not GMF interference. The third set of signals may be acquired during the MR scan and contains both MHE and GMF interference. Applying filtering and reconstructive procedures described in the Summary of Invention, diagnostic physiological signals may be reconstructed from those obtained during the MR scan.

Because the number of channels and their sampling rate are relatively high, the data are transmitted in two parallel data streams using two wireless transmitters. The first transmitter transmits 8 ECG channels, whereas the second transmits blood-pressure and pulse-oximetry channels. The data are time-stamped using time markers (periodic impulses) that are recorded using a dedicated reference channel in each data stream. These time markers are used by the receiving station to synchronize the two data streams by time-aligning the corresponding time markers.

Interventional CMR procedures often require X-ray imaging as well. For this purpose, patient table is quickly moved to an adjacent X-ray imaging room. Because a medical device of this invention is wireless, it does not restrict movement of the patient table and provides uninterrupted monitoring during patient transportation from the MR room to the X-ray room. To provide diagnostic-quality monitoring during an X-ray (fluoroscopy)-guided procedure (which does not have a high-level GMF), Filterbank II can be switched to Filterbank I.

Example 2

MRI-Guided Cardiac Electrophysiology Study

This hypothetical example describes the application of a medical device of this invention for an MR-guided cardiac electrophysiology study. The monitoring procedure is similar to that described in example 1. However, the system configuration required for this time-critical setting is different.

Example systems of this invention may use a wireless and/or non-wireless (e.g., USB cable) connection for transferring the data to a PC without delay (which is inherent for wireless transmission at 2.4 or 5.2 GHz). In some preferred embodiments, the system utilizes the data-acquisition and processing circuitry disclosed on FIG. 12 and FIG. 13 to minimize the EMI generated by the GMFs of an Mill scanner.

In some preferred embodiments, the system of this invention may utilize two parallel data streams passed through both Filterbanks I and II to allow clinicians to monitor interchangeably or concurrently signals passed through both filterbanks.

Example systems of this invention may utilize a wireless transmission architecture, in which all data channels are transmitted at two different frequencies (2.4 and 5.2 GHz), using two wireless transmitters, to ensure uninterrupted transmission of all data channels in this time-critical setting. This redundant transmission ensures that the receiving station receives all the data channels if one transmission frequency becomes unavailable or experiences a transmission delay.

Example 3

External Cardiac Defibrillation and Transcutaneous Pacing During MRI

This hypothetical example describes the application of a medical device of this invention for external cardiac defibrillation and transcutaneous pacing during MRI procedures. External defibrillation and electrical pacing are frequently required in the course of MR-guided electrophysiology procedures, when a cardiac arrhythmia is induced or occurs spontaneously and requires termination. In order to provide synchronized cardioversion (i.e., shock delivery synchronized with a specific part of the cardiac cycle, usually with ventricular depolarization, using the QRS complex or its R wave on the ECG as a time marker) and/or "demand" pacing (i.e., delivery of electrical pacing stimuli with simultaneous monitoring of the patient's intrinsic cardiac beats and inhibition/cessation of pacing in the presence of the patient's intrinsic cardiac activity), external defibrillators and/or pacing systems require continuous physiological monitoring in the presence of EMI generated by the MIll scanners.

Example systems of this inventions may include an accessory for an external defibrillator, which may be attached to the defibrillator (e.g., an accessory disclosed in Shusterman U.S. Patent Application 62/490,031). To provide EMI-free monitoring of physiological signals, the accessory may include the data-acquisition and processing circuitry disclosed on FIG. 12 and FIG. 13, which minimizes EMI in the monitored signals (e.g., ECG, blood pressure, and pulse oximetry).

In this hypothetic example, a ventricular tachyarrhythmia spontaneously occurs during an MR-guided electrophysiology study. External defibrillation is applied using a system of this invention (with an EMI-minimizing accessory disclosed in Shusterman U.S. Patent Application 62/490,031). The accessory provides uninterrupted monitoring of the physiological signals in the presence of EMI, before and after the defibrillation. By monitoring physiological signals (e.g., ECG, blood pressure, pulse oximetry) continuously, clinicians are able to track changes in cardiac waveforms and determine the type of cardiac rhythm. This is particularly important for determining the success or failure of each defibrillation attempt without delay.

Example 4

MRI of the Brain

This hypothetical example describes the application of a medical device of this invention for high-resolution brain imaging requiring data recording from up to 100 channels simultaneously, at a high sampling frequency. The monitoring and setup procedures are similar to those described in examples 1 and 2. However, because the number of monitoring channels is bigger, the system configuration is expanded to include ten data-acquisition modules with associated wireless transmitters, which are time-synchronized as described above.

Whereas particular aspects of the method of the present invention and particular embodiments of the invention have been described for purposes of illustration, it will be appreciated by those skilled in the art that numerous variations of the details may be made without departing from the invention as described in the appended claims.

The invention claimed is:

1. An accessory for attachment to a cardiac defibrillator that substantially minimizes EMI in at least one signal selected from signals received by said defibrillator and signals generated by said defibrillator, said accessory comprising:
at least one sensor adapted for collecting at least one input signal containing physiological data from the body of said individual;
at least one EMI detector based on at least one time-domain feature having a different range of values for said EMI compared with the range of values of said time-domain feature for said physiological data, to identify EMI waveforms within said at least one input signal; and
at least one processing element for minimizing said EMI within the time intervals in which said EMI is detected, in which said at least one processing element is selected from:

a. at least one delay line for holding said input signal during the time required for EMI detection;
b. at least one switch for performing at least two operations on the output signal from said at least one EMI detector, wherein said operations are selected from:
  i. passing said output signal from said at least one EMI detector to at least one data-acquisition element during the time intervals in which no EMI is detected; and
  ii. discarding said output signal during the time intervals in which EMI is detected;
c. at least one element for regulating the switching-on delay of said at least one switch respecting said EMI, which determines the duration of the discarded segment of said input signal;
d. at least one sample-and-hold element for holding the last value of said input signal preceding the time interval in which said EMI is detected; and
e. at least one filter element selected from:
  i. an RF filter respecting the Larmor frequency of the magnetic-field source generating said EMI; and
  ii. a low-pass filter respecting the difference between the frequency of said EMI and said physiological data for filtering residual noise and EMI from said input signal.

2. An accessory as set forth in claim 1 in which said at least one processing element for minimizing said EMI waveforms performs at least one operation selected from complete EMI blanking, partial EMI blanking, EMI clipping, EMI attenuation, EMI subtraction, and EMI filtering.

3. An accessory as set forth in claim 1 in which said at least one sensor is selected from an ECG sensor, an EMG sensor, an EEG sensor, a blood-pressure sensor, a pulse-oximetry sensor, and an accelerometer sensor.

4. An accessory as set forth in claim 1 in which said at least one EMI detector is selected from an edge detector, a level detector, a peak amplitude detector, a peak $1^{st}$ time derivative detector, a peak $2^{nd}$ time derivative detector, a detector for measuring the time interval between the peak EMI amplitude and at least one time derivative, and a detector for measuring the time interval between the peak $1^{st}$ derivative and the peak $2^{nd}$ derivative.

5. An accessory as set forth in claim 1 which further includes at least one control element selected from a control element of an edge-detector threshold and a control element of an amplitude-detector threshold.

6. An accessory as set forth in claim 1 in which said at least one processing element for minimizing said EMI waveforms includes at least one differential amplifier receiving reference voltage from at least one EMI level detector and subtracting said reference voltage from said at least one input signal.

7. An accessory as set forth in claim 1 in which said at least one EMI detector includes at least one edge detector and at least one level detector, and which further includes at least one logic element for performing at least one logical operation on the outputs of said edge detector and level detector to produce a single binary output.

8. An accessory as set forth in claim 1 which includes at least one wireless transmitter for transmitting said physiological data and at least one wireless receiving station for receiving said physiological data from said at least one wireless transmitter.

9. A method adapted for at least one health-related application selected from the physiological monitoring of an individual's health data, defibrillation, and pacing in the presence of EMI generated by an MRI scanner during an MRI scan of said individual, said method comprising:

collecting at least one input signal containing physiological data from the body of said individual;

detecting EMI within said at least one input signal based on at least one time-domain feature having a different range of values for EMI compared with the range of values of said time-domain feature for said physiological data, wherein said detecting is performed using at least one operation selected from edge detection, level detection, peak amplitude detection, peak $1^{st}$ time derivative detection, peak $2^{nd}$ time derivative detection, detection of the time interval between the peak EMI amplitude and at least one time derivative, and detection of the time interval between the peak $1^{st}$ derivative and the peak $2^{nd}$ derivative; and processing said at least one input signal to minimize said EMI within the time intervals in which said EMI is detected.

10. A method as set forth in claim 9 which includes regulation of at least one threshold selected from: an edge-detector threshold and an amplitude-detector threshold.

11. A method as set forth in claim 9 in which said detecting EMI waveforms includes at least two types of EMI detection and at least one logical operation on the outputs of said at least two types of EMI detection to produce a single binary output.

12. A method as set forth in claim 9 in which said input signal is selected from an ECG signal, EMG signal, EEG signal, pulse-oximetry signal, accelerometer signal, MR-based measurements of blood flow, arterial pressure-wave signal, blood-volume signal, intra-arterial blood-pressure signal, intra-cardiac blood-pressure signal, venous blood-pressure signal, noninvasively measured blood-pressure signal, photoplethysmographic signal, electrical-impedance signal, acoustic-wave signal, ultrasound signal, and infrared signal.

13. A method as set forth in claim 9 in which said processing includes at least one operation selected from complete EMI blanking, partial EMI blanking, EMI clipping, EMI attenuation, EMI subtraction and EMI filtering.

14. A method as set forth in claim 9 in which said processing includes receiving reference voltage from at least one EMI level detector and subtracting said reference voltage from said at least one input signal.

15. A method adapted for at least one health-related application selected from the physiological monitoring of an individual's health data, defibrillation, and pacing in the presence of EMI generated by an MRI scanner during an MRI scan of said individual, said method comprising:

collecting at least one input signal containing physiological data from the body of said individual;

detecting EMI within said at least one input signal based on at least one time-domain feature having a different range of values for EMI compared with the range of values of said time-domain feature for said physiological data; and processing said at least one input signal to minimize said EMI within the time intervals in which said EMI is detected in which said processing is selected from:

a. holding said at least one input signal during the time required for EMI detection;

b. performing at least two operations on the output signal from said EMI detection, wherein said operations are selected from:
  i. passing said output signal from said EMI detection to at least one data-acquisition component during the time intervals in which no EMI is detected; and
  ii. discarding said output signal during the time intervals in which EMI is detected;

c. switching-on delay after said EMI is detected to increase the duration of the discarded segment of said at least one input signal during EMI periods;

d. holding the last value of said at least one input signal preceding the time interval in which said EMI waveforms are detected; and e. filtering said at least one input signal using at least one filtering process selected from:
  i. RF filtering respecting the Larmor frequency of the magnetic-field source generating said EMI; and
  ii. low-pass filtering respecting the difference between the frequency of said EMI and said physiological data.

16. A method as set forth in claim 15 which further includes regulating the length of said switching-on delay following the time interval in which said EMI is detected.

17. A system adapted for at least one health-related application selected from the physiological monitoring of an individual's health data, cardiac defibrillation, and pacing in the presence of EMI generated by an MRI scanner during an MRI scan of said individual, said system comprising:

at least one sensor adapted for collecting at least one input signal containing physiological data from the body of said individual, wherein said at least one sensor is selected from an ECG sensor, an EMG sensor, an EEG sensor, a blood-pressure sensor, a pulse-oximetry sensor and an accelerometer sensor;

at least one EMI detector based on at least one time-domain feature having a different range of values for said EMI compared with the range of values of said time-domain feature for said physiological data, to identify EMI waveforms within said at least one input signal; and at least one processing element for minimizing said EMI within the time intervals in which said EMI is detected and which performs at least one operation selected from complete EMI blanking, partial EMI blanking, EMI clipping, EMI attenuation, EMI subtraction, and EMI filtering.

18. A system as set forth in claim 17 in which said at least one EMI detector includes at least one edge detector and at least one level detector, and which further includes at least one logic component for performing at least one logical operation on the outputs of said edge detector and level detector to produce a single binary output.

19. A system as set forth in claim 17 which includes at least one wireless transmitter for transmitting said physiological data and at least one wireless receiving station for receiving said physiological data from said at least one wireless transmitter.

* * * * *